(12) United States Patent
Wu et al.

(10) Patent No.: US 7,966,859 B2
(45) Date of Patent: Jun. 28, 2011

(54) UNDERFILL DETECTION SYSTEM FOR A BIOSENSOR

(75) Inventors: Huan-Ping Wu, Granger, IN (US);
Christine D. Nelson, Edwardsburg, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

(21) Appl. No.: 12/251,709

(22) Filed: Oct. 15, 2008

(65) Prior Publication Data

US 2009/0095071 A1 Apr. 16, 2009

Related U.S. Application Data

(63) Continuation of application No. PCT/US2007/068034, filed on May 2, 2007.

(60) Provisional application No. 60/797,128, filed on May 3, 2006.

(51) Int. Cl.
*G01N 27/26* (2006.01)
*G01N 27/00* (2006.01)
*G01N 33/487* (2006.01)

(52) U.S. Cl. ............................................. 73/1.02; 436/8
(58) Field of Classification Search .................... 73/1.02; 436/8
See application file for complete search history.

(56) References Cited

U.S. PATENT DOCUMENTS

| | | | |
|---|---|---|---|
| 4,431,004 A | 2/1984 | Bessman et al. | |
| 5,352,351 A | 10/1994 | White et al. | |
| 5,582,697 A | 12/1996 | Ikeda et al. | |
| 5,620,579 A | 4/1997 | Genshaw et al. | |
| 5,653,863 A | 8/1997 | Genshaw et al. | |
| 6,120,676 A | 9/2000 | Heller et al. | |
| 6,153,069 A | 11/2000 | Pottgen et al. | |
| 6,233,471 B1 | 5/2001 | Berner et al. | |
| 6,391,645 B1 | 5/2002 | Huang et al. | |
| 6,413,411 B1 | 7/2002 | Pottgen et al. | |
| 6,413,441 B1 | 7/2002 | Levin | |
| 6,448,067 B1 | 9/2002 | Tajnafoi | |
| 6,531,040 B2 | 3/2003 | Musho et al. | |
| 7,118,668 B1 * | 10/2006 | Edelbrock et al. | 205/777.5 |
| 7,122,110 B2 * | 10/2006 | Deng et al. | 205/777.5 |
| 2002/0084196 A1 | 7/2002 | Liamos et al. | |
| 2002/0146835 A1 | 10/2002 | Modzelewski et al. | |

(Continued)

FOREIGN PATENT DOCUMENTS

WO WO 03091717 4/2003

(Continued)

OTHER PUBLICATIONS

EPO, "Search Report and Written Opinion for PCT/US2007/068034", Sep. 24, 2007, Publisher: International Searching Authority.

*Primary Examiner* — Thomas P Noland
(74) *Attorney, Agent, or Firm* — Blanchard & Associates

(57) ABSTRACT

A biosensor has an underfill detection system that determines whether a sample of a biological fluid is large enough for an analysis of one or more analytes. The underfill detection system applies an excitation signal to the sample, which generates an output signal in response to the excitation signal. The underfill detection system switches the amplitude of the excitation signal. The transition of the excitation signal to a different amplitude changes the output signal when the sample is not large enough for an accurate and/or precise analysis. The underfill detection system measures and compares the output signal with one or more underfill thresholds to determine whether an underfill condition exists.

21 Claims, 10 Drawing Sheets

U.S. PATENT DOCUMENTS

| | | |
|---|---|---|
| 2002/0160517 A1 | 10/2002 | Modzelewski et al. |
| 2004/0256248 A1 | 12/2004 | Burke et al. |
| 2004/0259180 A1* | 12/2004 | Burke et al. ............... 435/14 |
| 2005/0023154 A1 | 2/2005 | Kermani et al. |
| 2005/0259180 A1 | 11/2005 | Su et al. |
| 2007/0045127 A1* | 3/2007 | Huang et al. ............... 205/777.5 |
| 2008/0173552 A1 | 7/2008 | Wu et al. |
| 2008/0179197 A1 | 7/2008 | Wu |
| 2009/0099787 A1* | 4/2009 | Carpenter et al. ............ 702/19 |

FOREIGN PATENT DOCUMENTS

| | | |
|---|---|---|
| WO | WO 2005073393 | 8/2005 |
| WO | WO 2005078437 | 8/2005 |
| WO | WO 2006079797 | 8/2006 |

* cited by examiner

UNDERFILL DETECTION SYSTEM FOR A BIOSENSOR

REFERENCE TO RELATED APPLICATIONS

This application is a continuation of PCT/US2007/68034 entitled "Underfill Detection System for a Biosensor" filed May 2, 2007, which was published in English and claimed the benefit of U.S. Provisional Application No. 60/797,128 entitled "Underfill Detection System for a Biosensor" filed May 3, 2006, which are incorporated by reference in their entirety.

BACKGROUND

Biosensors usually provide an analysis of a biological fluid, such as whole blood, urine, or saliva. Typically, a biosensor analyzes a sample of the biological fluid to determine the concentration of one or more analytes, such as glucose, uric acid, lactate, cholesterol, or bilirubin, in the biological fluid. The analysis is useful in the diagnosis and treatment of physiological abnormalities. For example, a diabetic individual may use a biosensor to determine the glucose level in blood for adjustments to diet and/or medication. When used, a biosensor may be underfilled if the sample size is not large enough. An underfilled biosensor may not provide an accurate analysis of the biological fluid.

Biosensors may be implemented using bench-top, portable, and like devices. The portable devices may be hand-held. Biosensors may be designed to analyze one or more analytes and may use different volumes of biological fluids. Some biosensors may analyze a single drop of whole blood, such as from 0.25-15 microliters ($\mu$L) in volume. Examples of portable measuring devices include the Ascensia Breeze® and Elite® meters of Bayer Corporation; the Precision® biosensors available from Abbott in Abbott Park, Ill.; Accucheck® biosensors available from Roche in Indianapolis, Ind.; and OneTouch Ultra® biosensors available from Lifescan in Milpitas, Calif. Examples of bench-top measuring devices include the BAS 100B Analyzer available from BAS Instruments in West Lafayette, Ind.; the CH Instruments' Electrochemical Workstation available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J.

Biosensors usually measure an electrical signal to determine the analyte concentration in a sample of the biological fluid. The analyte typically undergoes an oxidation/reduction or redox reaction when an excitation signal is applied to the sample. An enzyme or similar species may be added to the sample to enhance the redox reaction. The excitation signal usually is an electrical signal, such as a current or potential. The redox reaction generates an output signal in response to the excitation signal. The output signal usually is an electrical signal, such as a current or potential, which may be measured and correlated with the concentration of the analyte in the biological fluid.

Many biosensors have a measuring device and a sensor strip. A sample of the biological fluid is introduced into a sample chamber in the sensor strip. The sensor strip is placed in the measuring device for analysis. The measuring device usually has electrical contacts that connect with electrical conductors in the sensor strip. The electrical conductors typically connect to working, counter, and/or other electrodes that extend into a sample chamber. The measuring device applies the excitation signal through the electrical contacts to the electrical conductors in the sensor strip. The electrical conductors convey the excitation signal through the electrodes into a sample deposited in the sample chamber. The redox reaction of the analyte generates an output signal in response to the excitation signal. The measuring device determines the analyte concentration in response to the output signal.

The sensor strip may include reagents that react with the analyte in the sample of biological fluid. The reagents may include an ionizing agent for facilitating the redox of the analyte, as well as mediators or other substances that assist in transferring electrons between the analyte and the conductor. The ionizing agent may be an analyte specific enzyme, such as glucose oxidase or glucose dehydrogenase, which catalyze the oxidation of glucose in a whole blood sample. The reagents may include a binder that holds the enzyme and mediator together.

Biosensors may include an underfill detection system to prevent or screen out analyses associated with sample sizes that are of insufficient volume. Because concentration values obtained from an underfilled sensor strip may be inaccurate, the ability to prevent or screen out these inaccurate analyses may increase the accuracy of the concentration values obtained. Some underfill detection systems have one or more indicator electrodes that detect the partial and/or complete filling of a sample chamber within a sensor strip. The indicator electrode(s) may be separate or part of the working, counter, or other electrodes used to determine the concentration of analyte in the sample. An electrical signal usually passes through the indicator electrode(s) when a sample is present in the sample chamber. The electrical signal may be used to indicate whether a sample is present and whether the sample partially or completely fills the sample chamber.

Some biosensors have a third or indicator electrode in addition to the counter and working electrodes used to apply an excitation signal to a sample of the biological fluid. The third electrode may be positioned to detect whether the sample forms a liquid junction between the electrodes. In operation, a potential is applied between the third electrode and the counter electrode. When the sample connects the electrodes, current flows between the third and counter electrodes. The biosensor detects the current to determine whether the sensor strip is filled. A biosensor using an underfill detection system with a third electrode is described in U.S. Pat. No. 5,582,697.

Other biosensors use a sub-element of the counter electrode to determine whether the sensor strip is underfilled. The sub-element may be located upstream from the working electrode, where only the sub-element is in electrical communication with the working electrode when the sensor strip is underfilled. In operation, an insufficient flow of current between the sub-element and the working electrode occurs when the sensor strip is underfilled. The biosensor detects the insufficient flow of current and provides an error signal indicating the sensor strip is underfilled. A biosensor using an underfill detection system with a sub-element of the counter electrode is described in U.S. Pat. No. 6,531,040.

While these underfill detection systems balance various advantages and disadvantages, none are ideal. These systems usually include additional components, such as the indicator electrodes. The additional components may increase the manufacturing cost of the sensor strip. The additional components also may introduce additional inaccuracy and imprecision due to the variability of manufacturing processes.

In addition, these systems may require a larger sample chamber to accommodate the indicator electrodes. The larger sample chamber may increase the sample size needed for an accurate and precise analysis of the analyte.

Moreover, these systems may be affected by uneven or slow filling of the sample chamber. The uneven or slow filling may cause these systems to indicate that the sensor strip is underfilled when the sample size is large enough. The uneven or slow filling also may cause these systems to indicate the sensor strip is filled when the sample size is not large enough.

These systems also may not detect that the sensor strip is underfilled early enough to add more of the biological fluid. The delay may require replacing the sensor strip with a new sensor strip and a new sample of the biological fluid.

Accordingly, there is an ongoing need for improved biosensors, especially those that may provide increasingly accurate and/or precise detection of underfilled sensor strips. The systems, devices, and methods of the present invention overcome at least one of the disadvantages associated with conventional biosensors.

SUMMARY

A biosensor with an underfill detection system determines whether a sample of a biological fluid is large enough for an analysis of one or more analytes. The underfill detection system measures a test output signal from the sample in response to test excitation signal. The underfill detection system switches the test excitation signal to one or more different amplitudes. The transition to one or more different amplitudes changes the test output signal from the sample in response to an underfill condition.

In a method for detecting an underfill condition in a biosensor, a test excitation signal is applied to a sample of a biological fluid. The test excitation signal is switched to one or more different amplitudes. A test output signal from the sample is measured. The test output signal is compared with one or more underfill thresholds.

In another method for detecting an underfill condition in a biosensor, a polling excitation signal is applied to a sample of a biological fluid. A test excitation signal is applied to the sample when a polling output signal from the sample is equal to or greater than a polling threshold. The test excitation signal is switched to one or more different amplitudes. A test output signal from the sample is measured. The test output signal is compared with one or more underfill thresholds. An error signal is generated.

A biosensor for determining an analyte concentration in a biological fluid may have a sensor strip and a measuring device. The sensor strip may have a sample interface on a base. The sample interface is adjacent to a reservoir formed by the base. The measuring device may have a processor connected to a sensor interface. The sensor interface may have electrical communication with the sample interface. The processor applies a test excitation signal to the sample interface. The processor switches the test excitation signal to one or more different amplitudes. The processor measures a test output signal from the sample interface. The processor compares the test output signal to one or more underfill thresholds.

A method, for detecting an underfill condition in a biosensor, includes applying a test excitation signal to a sample of a biological fluid, switching the test excitation signal to at least one different amplitude, measuring a test output signal from the sample, and comparing the test output signal with at least one underfill threshold. The test excitation signal may be part of an assay excitation signal in an electrochemical sensor system. The test excitation signal may have a test pulse width in the range of about 0.1 sec through about 3 sec and a test pulse interval in the range of about 0.2 sec through about 6 sec. The method may apply the test excitation signal during a test period of less than about 180 sec. The test period may be in the range of about 1 sec through about 100 sec. The method may include applying the test excitation signal during a test period having test pulse intervals in the range of about 2 through about 50.

The detection method may include switching the test excitation signal to at least one different amplitude essentially at a start of the test excitation signal, to at least one different amplitude during a test pulse, and/or to at least one different amplitude during a transition from one test pulse to another test pulse. The method may include switching the test excitation signal to a first different amplitude during a test pulse and switching the test excitation signal to a second different amplitude during a transition from one test pulse to another test pulse. The method may include decreasing the amplitude essentially at the start of the test excitation signal, decreasing the amplitude of the test excitation signal during the transition from one test pulse to another test pulse, and/or decreasing the amplitude the test excitation signal multiple times.

The detection method may include generating a decrease in the test output signal in response to an underfill condition and/or generating an error signal in response to an underfill condition. The method may request the addition of biological fluid to the sample in response to the error signal and/or stop the analysis.

The detection method may include detecting when a sample of a biological fluid is available for analysis and may apply a polling excitation signal to the sample. The test excitation signal may be switched to a different amplitude than the polling excitation signal. A polling output signal may be generated in response to the polling excitation signal and the test excitation signal may be applied to the sample when the polling output signal is equal to or greater than a polling threshold.

The at least one different amplitude of the method may be lower than an original amplitude. The original and different amplitudes may be selected from an output signal plateau in an electrochemical sensor system. The output signal plateau may include excitation amplitudes that generate output signals within ±5% of an average output signal.

A method for detecting an underfill condition in a biosensor includes applying a polling excitation signal to a sample of a biological fluid, applying a test excitation signal to the sample when a polling output signal from the sample is equal to or greater than a polling threshold, switching the test excitation signal to at least one different amplitude, measuring a test output signal from the sample, comparing the test output signal with at least one underfill threshold, and generating an error signal. The polling excitation signal may have a polling pulse width of less than about 300 ms and a polling pulse interval of less than about 1 sec. The polling excitation signal may have a polling pulse width in the range of about 0.5 ms through about 75 ms and may have a polling pulse interval in the range of about 5 ms through about 300 ms. The test excitation signal may have a test pulse width of less than about 5 sec and a test pulse interval of less than about 15 sec. The test excitation signal may have a test pulse width in the range of about 0.1 sec through about 3 sec and have a test pulse interval in the range of about 0.2 sec through about 6 sec. The polling excitation signal may have at least one polling pulse with an amplitude of about 400 mV, and the test excitation signal may have at least one test pulse with an amplitude of about 200 mV.

The at least one different amplitude may be lower than an original amplitude and the original amplitude may be an amplitude of the polling excitation signal. The original and different amplitudes may be selected from an output signal plateau in an electrochemical sensor system. The output signal plateau may include excitation amplitudes that generate output signals within ±5% of an average output signal.

The method also may include applying the polling excitation signal during a polling period of less than about 180 sec and applying the test excitation signal during a test period of less than about 180 sec. This method may include applying the polling excitation signal during a polling period in the range of about 0.1 sec through about 10 sec and applying the test excitation signal during a test period in the range of about 1 sec through about 100 sec.

The method also may include switching the test excitation signal to at least one different amplitude essentially at a start of the test excitation signal, switching the test excitation signal to at least one different amplitude during a test pulse, and/or switching the test excitation signal to at least one different amplitude during a transition from one test pulse to another test pulse. The method also may include switching the test excitation signal to a first different amplitude during a test pulse and switching the test excitation signal to a second different amplitude during a transition from one test pulse to another test pulse.

The method also may include decreasing the amplitude essentially at the start of the test excitation signal, decreasing the amplitude of the test excitation signal during the transition from one test pulse to another test pulse, and/or decreasing the amplitude the test excitation signal multiple times. The method also may include generating a decrease in the test output signal in response to an underfill condition, decreasing the test output signal in response to an underfill condition, and/or generating a negative test output signal in response to an underfill condition.

The test output signal may indicate an underfill condition when the test output signal is equal to or less than a first underfill threshold, and where the test output signal indicates an underfill condition when a change in the test output signal is equal to or greater than a second underfill threshold. The method also may include requesting the addition of biological fluid to the sample in response to the error signal and/or stopping an analysis of an analyte in the sample in response to the error signal. The test excitation signal may be part of an assay excitation signal in an electrochemical sensor system.

A biosensor, for determining an analyte concentration in a biological fluid, including a sensor strip having a sample interface on a base, where the sample interface is adjacent to a reservoir formed by the base, a measuring device having a processor connected to a sensor interface, where the sensor interface has electrical communication with the sample interface, and where the processor applies a test excitation signal to the sample interface, the processor switches the test excitation signal to at least one different amplitude, the processor measures a test output signal from the sample interface, and the processor compares the test output signal to at least one underfill threshold. The processor may apply a polling excitation signal to the sample. The processor may switch from the polling excitation signal to the test excitation signal when the polling output signal is equal to or greater than a polling threshold. The processor may apply the polling excitation signal during a polling period of less than 180 seconds and may apply the test excitation signal during a test period of less than 180 seconds.

The polling excitation signal may have a polling pulse width in the range of about 0.5 ms through about 75 ms and the polling excitation signal may have a polling pulse interval in the range of about 5 ms through about 300 ms. The test excitation signal may have a test pulse width less than about 5 sec and a test pulse interval less than about 15 sec. The at least one different amplitude may be lower than an original amplitude. The original amplitude may be an amplitude of a polling excitation signal. The original and different amplitudes may be selected from an output signal plateau in an electrochemical sensor system and the output signal plateau may include excitation amplitudes that generate output signals within ±5% of an average output signal.

The processor of the biosensor may switch the test excitation signal to at least one different amplitude essentially at a start of the test excitation signal. The processor may switch the test excitation signal to at least one different amplitude during a test pulse and/or may switch the test excitation signal to at least one different amplitude during a transition from one test pulse to another test pulse. The processor may switch the test excitation signal to a first different amplitude during a test pulse and may switch the test excitation signal to a second different amplitude during a transition from one test pulse to another test pulse. The processor may reduce the amplitude of at least one test pulse in the test excitation signal below the amplitude of a polling pulse in the polling excitation signal. The test excitation signal may be part of an assay excitation signal in an electrochemical sensor system.

The biosensor may include a display connected to the processor, where the processor shows an error signal on the display in response to an underfill condition. The error signal may request the user to add biological fluid to the sample in response to the error signal and/or the processor may stop the analysis of the analyte in the sample in response to the error signal. The sample interface may have a counter electrode and a working electrode, the counter electrode may have a sub-element.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

The present invention provides an underfill detection system for a biosensor. The underfill detection system improves the accuracy and precision of the biosensor in determining whether a sample of a biological fluid is large enough for an analysis of one or more analytes. The underfill detection system applies a test excitation signal to a sample deposited in the biosensor. The test excitation signal is switched to one or more different amplitudes. The sample generates a test output signal in response to the test excitation signal. The transition of the test excitation signal to a different amplitude changes the test output signal when the sample is not large enough for an accurate and/or precise analysis. The underfill detection system measures and compares the test output signal with one or more underfill thresholds to determine whether an underfill condition exists. The biosensor may be utilized to determine one or more analyte concentrations, such as glucose, uric acid, lactate, cholesterol, bilirubin, or the like, in a biological fluid, such as whole blood, urine, saliva, or the like.

Figure 1:
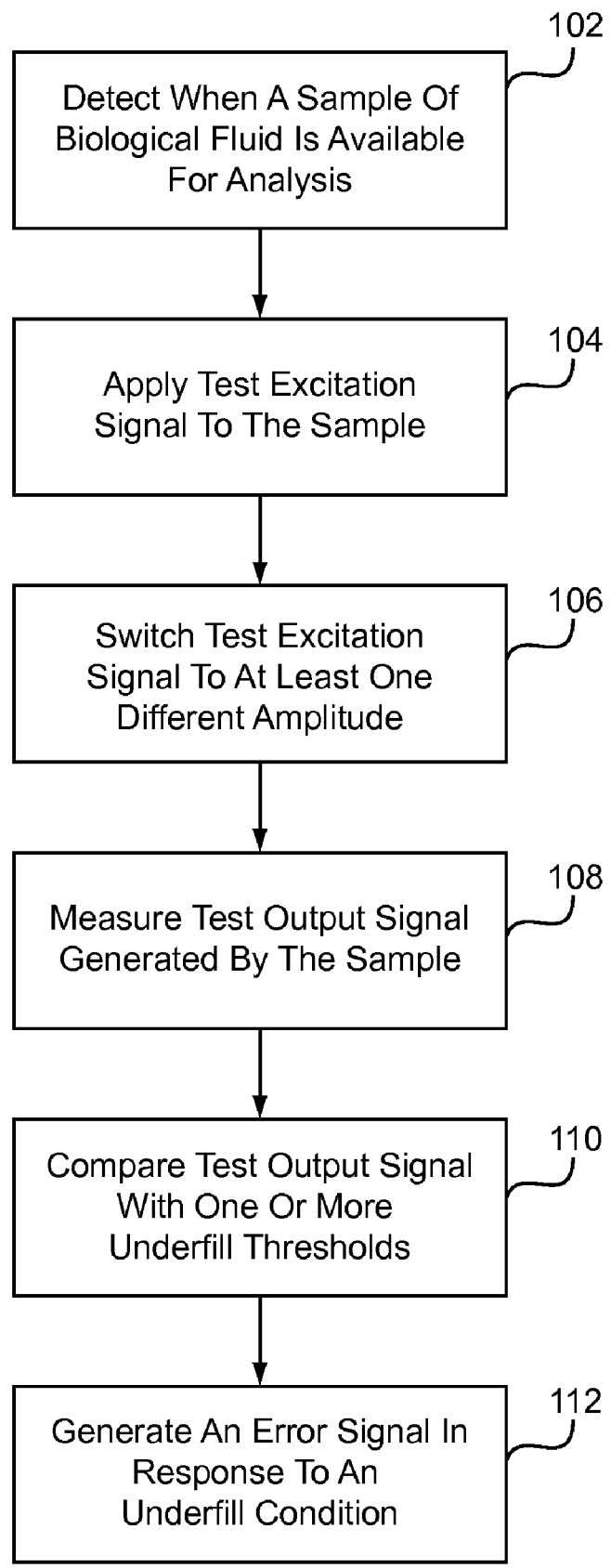
FIG. 1 represents a method for detecting an underfill condition in a biosensor.

FIG. 1 represents a method for detecting an underfill condition in a biosensor. In 102, the biosensor detects when a sample of a biological fluid is available for analysis. In 104, the biosensor applies a test excitation signal to the sample. In 106, the biosensor switches the test excitation signal to at least one different amplitude. In 108, the biosensor measures the test output signal generated by the sample in response to the test excitation signal. In 110, the biosensor compares the test output signal with one or more underfill thresholds. In 112, the biosensor generates an error signal or other indication in response to an underfill condition when the test output signal indicates the sample size is not large enough.

In 102 of FIG. 1, the biosensor detects when a sample of a biological fluid is available for analysis. The biosensor may sense when a sensor strip is placed in a measuring device. The biosensor may sense (mechanically, electrically, or the like) when electrical contacts in the measuring device connect with electrical conductors in the sensor strip. The biosensor may apply a polling excitation signal or other sensing signal to the working, counter, and/or other electrodes to detect when a sample connects with the electrodes. The biosensor may use other methods and devices to detect when a sample is available for analysis.

The polling excitation signal is an electrical signal, such as current or potential, that pulses or turns on and off at a set frequency or interval. The sample generates a polling output signal in response to the polling excitation signal. The polling output signal is an electrical signal, such as current or poten-tial. The biosensor may show the polling output signal on a display and/or may store the test output signal in a memory device.

The polling excitation signal is a sequence of polling pulses separated by polling relaxations. During a polling pulse, the electrical signal is on. During a polling relaxation, the electrical signal is off. On may include time periods when an electrical signal is present. Off may include time periods when an electrical signal is not present. Off may not include time periods when an electrical signal is present but has essentially no amplitude. The electrical signal may switch between on and off by closing and opening an electrical circuit, respectively. The electrical circuit may be opened and closed mechanically, electrically, or the like.

A polling excitation signal may have one or more polling pulse intervals. A polling pulse interval is the sum of a polling pulse and a polling relaxation. Each polling pulse has an amplitude and a polling pulse width. The amplitude indicates the intensity of the potential, the current, or the like of the electrical signal. The amplitude may vary or be a constant during the polling pulse. The polling pulse width is the time duration of a polling pulse. The polling pulse widths in a polling excitation signal may vary or be essentially the same. Each polling relaxation has a polling relaxation width, which is the time duration of a polling relaxation. The polling relaxation widths in a polling excitation signal may vary or be essentially the same.

The polling excitation signal may have a polling pulse width of less than about 300 milliseconds (ms) and a polling pulse interval of less than about 1 sec. The polling excitation signal may have a polling pulse width of less than about 100 ms and a polling pulse interval of less than about 500 ms. The polling excitation signal may have a polling pulse width in the range of about 0.5 ms through about 75 ms and a polling pulse interval in the range of about 5 ms through about 300 ms. The polling excitation signal may have a polling pulse width in the range of about 1 ms through about 50 ms and a polling pulse interval in the range of about 10 ms through about 250 ms. The polling excitation signal may have a polling pulse width of about 5 ms and a polling pulse interval of about 125 ms. The polling excitation signal may have other pulse widths and pulse intervals.

The biosensor may apply the polling excitation signal to the sample during a polling period. The polling period may be less than about 15 minutes, 5 minutes, 2 minutes, or 1 minute. The polling period may be longer depending upon how a user uses the biosensor. The polling period may be in the range of about 0.5 second (sec) through about 15 minutes. The polling period may be in the range of about 5 sec through about 5 minutes. The polling period may be in the range of about 10 sec through about 2 minutes. The polling period may be in the range of about 20 sec through about 60 sec. The polling period may be in the range of about 30 through about 40 sec. The polling period may have less than about 200, 100, 50, or 25 pulse intervals. The polling period may have from about 2 through about 150 pulse intervals. The polling period may have from about 5 through about 50 pulse intervals. The polling period may have from about 5 through about 15 pulse intervals. The polling period may have about 10 pulse intervals. Other polling periods may be used.

In 104 of FIG. 1, the biosensor applies a test excitation signal to the sample. The biosensor applies the test excitation signal when the polling output signal is equal to or greater than a polling threshold. The polling threshold may be greater than about 5 percent (%) of the expected test excitation signal at the beginning of the first pulse. The polling threshold may be greater than about 15% of the expected test excitation signal at the beginning of the first pulse. The polling threshold may be in the range of about 5 percent (%) through about 50% of the expected test excitation signal at the beginning of the first pulse. Other polling thresholds may be used. The biosensor may indicate the polling output signal is equal to or greater than the polling threshold on a display.

The test excitation signal is an electrical signal, such as current or potential, that pulses or turns on and off at a set frequency or interval. The sample generates a test output signal in response to the test excitation signal. The test output signal is an electrical signal, such as current or potential.

The test excitation signal is a sequence of test pulses separated by test relaxations. During a test pulse, the electrical signal is on. During a test relaxation, the electrical signal is off. On includes time periods when an electrical signal is present. Off includes time periods when an electrical signal is not present and does not include time periods when an electrical signal is present but has essentially no amplitude. The electrical signal switches between on and off by closing and opening an electrical circuit, respectively. The electrical circuit may be opened and closed mechanically, electrically, or the like.

A test excitation signal may have one or more test pulse intervals. A test pulse interval is the sum of a test pulse and a test relaxation. Each test pulse has an amplitude and a test pulse width. The amplitude indicates the intensity of the potential, the current, or the like of the electrical signal. The amplitude may vary or be a constant during the test pulse. The test pulse width is the time duration of a test pulse. The test pulse widths in a test excitation signal may vary or be essentially the same. Each test relaxation has a test relaxation width, which is the time duration of a test relaxation. The test relaxation widths in a test excitation signal may vary or be essentially the same.

The test excitation signal may have a test pulse width of less than about 5 sec and a test pulse interval of less than about 15 sec. The test excitation signal may have a test pulse width of less than about 3, 2, 1.5, or 1 sec and a test pulse interval of less than about 13, 7, 4, 3, 2.5, or 1.5 sec. The test excitation signal may have a test pulse width in the range of about 0.1 sec through about 3 sec and a test pulse interval in the range of about 0.2 sec through about 6 sec. The test excitation signal may have a test pulse width in the range of about 0.1 sec through about 2 sec and a test pulse interval in the range of about 0.2 sec through about 4 sec. The test excitation signal may have a test pulse width in the range of about 0.1 sec through about 1.5 sec and a test pulse interval in the range of about 0.2 sec through about 3.5 sec. The test excitation signal may have a test pulse width in the range of about 0.4 sec through about 1.2 sec and a test pulse interval in the range of about 0.6 sec through about 3.7 sec. The test excitation signal may have a test pulse width in the range of about 0.5 sec through about 1.5 sec and a test pulse interval in the range of about 0.75 sec through about 2.0 sec. The test excitation signal may have a test pulse width of about 1 sec and a test pulse interval of about 1.5 sec. The test excitation signal may have other pulse widths and pulse intervals.

The biosensor applies the test excitation signal to the sample during a test period. The test period may have the same or a different duration than the polling period. The test excitation signal may be part of an assay excitation signal used in an electrochemical sensor system. The test excitation signal and the assay excitation signal may be essentially the same signal. The test period of the test excitation signal may have the same or different duration as the assay excitation signal.

The test period of the test excitation signal may be less than about 180, 120, 90, 60, 30, 15, 10, or 5 sec. The test period may be in the range of about 1 sec through about 100 sec. The test period may be in the range of about 1 sec through about 25 sec. The test period may be in the range of about 1 sec through about 10 sec. The test period may be in the range of about 2 sec through about 3 sec. The test period may be about 2.5 sec. The test period may have less than about 50, 25, 20, 15, 10, 8, 6, or 4 test pulse intervals. The test period may have test pulse intervals in the range of about 2 through about 50. The test period may have test pulse intervals in the range of about 2 through about 25. The test period may have test pulse intervals in the range of about 2 through about 15. The test period may have about 10 test pulse intervals. Other test periods may be used.

In 106 of FIG. 1, the biosensor switches the test excitation signal to at least one different amplitude. When switching to a different amplitude, the biosensor may apply a test excitation signal with a different amplitude than the amplitude of the polling excitation signal. When switching to a different amplitude, the biosensor may apply a test excitation signal having one or more test pulses with different amplitudes. When switching to a different amplitude, the biosensor may apply a test excitation signal having one or more test pulses where the amplitude varies or shifts between different amplitudes. The biosensor may switch the amplitude of the test excitation signal essentially when the biosensor switches from the polling excitation signal to the test excitation signal. The biosensor may switch the amplitude of the test excitation signal essentially at the start of the test excitation signal. The biosensor may switch the test excitation signal to a different amplitude during a test pulse, during the transition from one test pulse to another test pulse, or the like. During a test pulse includes the start of the test pulse, the end of the test pulse, and any portion in between the start and end of the test pulse. During a test pulse includes any position or time from the start of the test pulse to the end of the test pulse. During a transition from one test pulse to another test pulse includes any position or time from the end of one test pulse to the start of another test pulse. During a transition from one test pulse to another test pulse includes any position or time that is part of or include in a test relaxation. The biosensor may switch the amplitude of the test excitation signal multiple times. The biosensor may switch the test output signal to a first different amplitude and later switch to a second different amplitude. Other switches in the amplitude of the test excitation signal may occur.

A different amplitude may be any amplitude that is essentially not the same as an original amplitude. The different amplitude may be higher or lower than the original amplitude. The different amplitude is the amplitude of the test excitation signal after a switch has occurred. An original amplitude is the amplitude prior to the switch. The original amplitude may be the amplitude of the polling excitation signal, the first or another test pulse in the test excitation signal, or the like. Other original and different amplitudes may be used.

A higher amplitude may be up to about 400% greater than the original amplitude. A higher amplitude may be in the range of about 2% through about 200% greater than the original amplitude. A higher amplitude may be in the range of about 5% through about 100% greater than the original amplitude. A higher amplitude may be in the range of about 25% through about 75% greater than the original amplitude. A higher amplitude may be about 50% greater than the original amplitude. Other higher amplitudes may be used.

A lower amplitude may be in the range of about 2% through about 98% less than the original amplitude. A lower amplitude may be in the range of about 5% through about 95% less than the original amplitude. A lower amplitude may be in the range of about 100% through about 90% less than the original amplitude. A lower amplitude may be in the range of about 20% through about 80% less than the original amplitude. A lower amplitude may be in the range of about 25% through about 65% less than the original amplitude. A lower amplitude may be about 50% less than the original amplitude. Other lower amplitudes may be used.

Each switch to a different amplitude may generate a change in the test output signal in response to an underfill condition. The change in the test output signal may include test output signals that are or become stronger or weaker than the test output signal when there is no underfill condition. The change in the test output signal may occur essentially at the same time and/or after the switch to a different amplitude occurs. The change in the test output signal may be measurable and may last for more than about 1 sec. When the amplitude of the test excitation signal is changed multiple times, each transition from or to a different amplitude may generate a further change in the test output signal.

The change in the test output signal may be a shift to the stronger or weaker test output signal. The shift may be essentially instantaneous, gradual, a combination thereof, or the like. A stronger test output signal has a greater or higher intensity than a weaker test output signal. For example, a test output signal of 2000 nanoAmperes (nA) is stronger or greater than a test output signal of 1200 nA. For example, a test output signal of −1100 nA is weaker or less than a test output signal of 1000 nA. Other test output signals may be used.

A switch to a lower amplitude may generate a decrease in the test output signal in response to an underfill condition. A decrease in the test output signal may occur essentially at the start of the test output signal such as when the test excitation signal starts or when the polling excitation signal switches to the test excitation signal. A decrease in the test output signal may occur when the test output signal becomes weaker or less after a switch of the test excitation signal to a different amplitude. The switch to a lower amplitude may generate a negative test output signal or a test output signal that becomes negative.

A switch to a higher amplitude may generate an increase in the test output signal in response to an underfill condition. An increase in the test output signal may occur essentially at the start of the test output signal such as when the test excitation signal starts or when the polling excitation signal switches to the test excitation signal. An increase in the test output signal may occur when the test output signal becomes stronger or greater after a switch of the test excitation signal to a different amplitude.

The original and different amplitudes may be selected to provide a more measurable or cleaner change in the test output signal when an underfill condition exists. The original and different amplitudes may selected to provide a change in the test output signal that is more independent of other conditions during the analysis of the sample. The original and different amplitudes may be selected so there is little or no change in the redox reaction of the analyte in the sample when amplitude transitions occur. In addition, the difference in the original and different amplitudes may be selected to increase or decrease the reduction in the test output signal when an underfill condition exists.

The original and different amplitudes may be selected from excitation amplitudes within an output signal plateau of the mediator in an electrochemical sensor system. A switch from one excitation amplitude to another excitation amplitude in the output signal plateau may generate little or no change in the redox reaction of the analyte in the sample. The output signal plateau may include excitation amplitudes where the electrochemical sensor system generates essentially the same or constant output signals. The output signal plateau may include excitation amplitudes where the electrochemical sensor system generates output signals within 1% of an average output signal or a selected output signal for the output signal plateau. The output signal plateau may include excitation amplitudes where the electrochemical sensor system generates output signals within ±5% of an average output signal or a selected output signal for the output signal plateau. The output signal plateau may include excitation amplitudes where the electrochemical sensor system generates output signals within ±10% of an average output signal or a selected output signal for the output signal plateau. Other output signal plateaus may be used.

Figure 2:
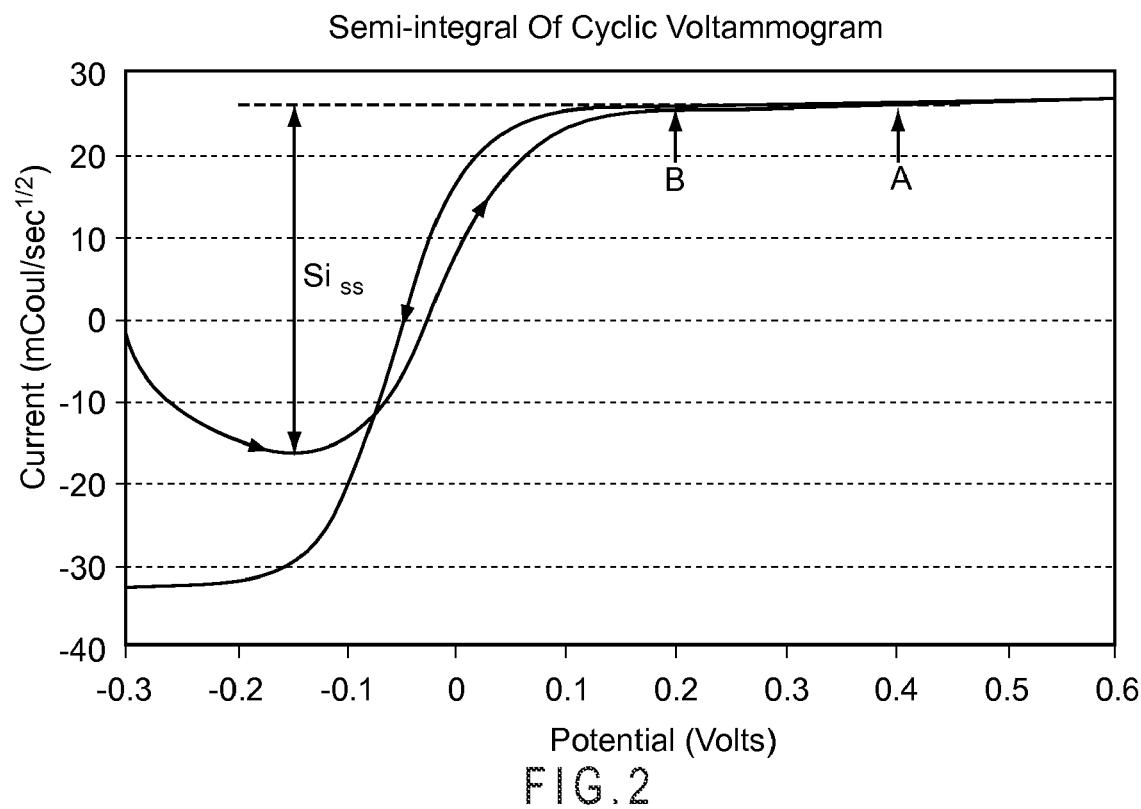
FIG. 2 is a graph illustrating a semi-integral of a cyclic voltammogram for a ferri/ferrocyanide redox couple.

FIG. 2 is a graph illustrating a semi-integral of a cyclic voltammogram for a ferri/ferrocyanide redox couple compared against the same ferri/ferrocyanide redox couple at the counter electrode. The semi-integral represents the current as a function of the applied potential in an electrochemical sensor system using a voltammetry or gated voltammetry electrochemical sensor system. The ferri/ferrocyanide redox couple is a mediator that assists with the oxidation and reduction of the analyte in the sample. Other redox couples may be used.

The semi-integral defines a current plateau in a range from about 0.18 volts (V) through about 0.6 V, where the current is essentially constant at about 27 micro-Coulombs per the square root of seconds ($\mu Coul/sec^{1/2}$). Within the current plateau, there is little or no change in the faradaic reaction—the transfer of electrons between the analyte and mediator and the electrodes in the biosensor. Only a charging current is generated due to the change in potential. The original and different amplitudes may be selected from potentials within the current plateau. An amplitude or potential of about 0.4 V (A in FIG. 2) for the original amplitude may be selected. The original amplitude may be the amplitude of polling pulse in a polling excitation signal or a test pulse in a test excitation signal. An amplitude or potential of about 0.2 V (B in FIG. 2) for the different amplitude may be selected. The different amplitude may be the amplitude of a test pulse or a portion of a test pulse in a test excitation signal. Other original and different amplitudes may be selected from the current plateau.

In 104 and 106 of FIG. 1, the polling and test signals may be part of or an addition to an electrochemical or optical sensor system used to determine one or more analyte concentrations in a sample of biological fluid. In electrochemical and optical sensor systems, an oxidation/reduction or redox reaction of an analyte in the sample generates an assay output signal. An enzyme or similar species may be added to the sample to enhance the redox reaction. The assay output signal is measured and correlated to the concentration of the analyte in the sample.

Optical sensor systems generally measure the amount of light absorbed or generated by the reaction of a chemical indicator with the analyte redox reaction. An enzyme may be included with the chemical indicator to enhance the reaction kinetics. The assay output signal or light from an optical system may be converted into an electrical signal such as current or potential.

In light-absorption optical systems, the chemical indicator produces a reaction product that absorbs light. An incident excitation beam from a light source is directed toward the sample. The incident beam may be reflected back from or transmitted through the sample to a detector. The detector collects and measures the attenuated incident beam (assay output signal). The amount of light attenuated by the reaction product is an indication of the analyte concentration in the sample.

In light-generated optical systems, the chemical detector fluoresces or emits light in response to the analyte redox reaction. A detector collects and measures the generated light (assay output signal). The amount of light produced by the chemical indicator is an indication of the analyte concentration in the sample.

Electrochemical sensor systems apply an assay excitation signal to the sample of the biological fluid. The assay excitation signal may be a potential or current and may be constant, variable, or a combination thereof such as when an AC signal is applied with a DC signal offset. The assay excitation signal may be applied as a single pulse or in multiple pulses, sequences, or cycles. The analyte undergoes a redox reaction when the assay excitation signal is applied to the sample. An enzyme or similar species may be used to enhance the redox reaction of the analyte. A mediator may be used to maintain the oxidation state of the enzyme. The redox reaction generates an assay output signal that may be measured constantly or periodically during transient and/or steady-state output. Various electrochemical processes may be used such as amperometry, coulometry, voltammetry, gated amperometry, gated voltammetry, and the like.

In amperometry, a potential or voltage is applied to a sample of the biological fluid. The redox reaction of the analyte generates a current in response to the potential. The current is measured at a fixed time at a constant potential to quantify the analyte in the sample. Amperometry generally measures the rate at which the analyte is oxidized or reduced to determine the analyte concentration in the sample. Biosensor systems using amperometry are described in U.S. Pat. Nos. 5,620,579; 5,653,863; 6,153,069; and 6,413,411.

In coulometry, a potential is applied to a sample of the biological fluid to exhaustively oxidize or reduce the analyte within the sample. The potential generates a current that is integrated over the time of oxidation/reduction to produce an electrical charge representing the analyte concentration. Coulometry generally captures the total amount of analyte within the sample. A biosensor system using coulometry for whole blood glucose measurement is described in U.S. Pat. No. 6,120,676.

In voltammetry, a varying potential is applied to a sample of biological fluid. The redox reaction of the analyte generates current in response to the applied potential. The current is measured as a function of applied potential to quantify the analyte in the sample. Voltammetry generally measures the rate at which the analyte is oxidized or reduced to determine the analyte concentration in the sample. Additional information about voltammetry may be found in "Electrochemical Methods: Fundamentals and Applications" by A. J. Bard and L. R. Faulkner, 1980.

In gated amperometry and gated voltammetry, pulsed excitations may be used as described in U.S. Provisional Patent Application Nos. 60/700,787, filed Jul. 20, 2005, and 60/722,584, filed Sep. 30, 2005, respectively, which are incorporated by reference.

The test excitation and output signals may be incorporated with the pulsed excitation and output signals of an electrochemical sensor system. The test excitation signal may be part of the assay excitation signal applied to a sample in gated amperometry or gated voltammetry systems. The test excitation signal may be the portion of the assay excitation signal that is applied to the sample during the test period. The test output signal may be the portion of the assay output signal generated by a sample during the test period. The test excitation and output signals may be incorporated with other electrochemical sensor systems.

Figure 3:
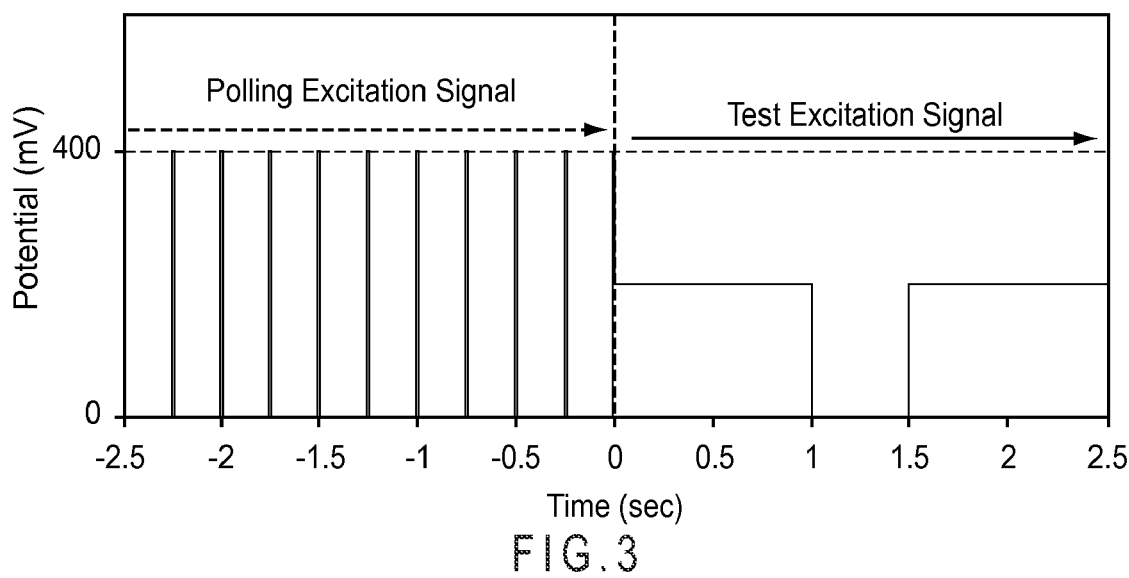
FIG. 3 is a graph illustrating an amplitude reduction at the beginning of the test excitation signal.
Figure 4:
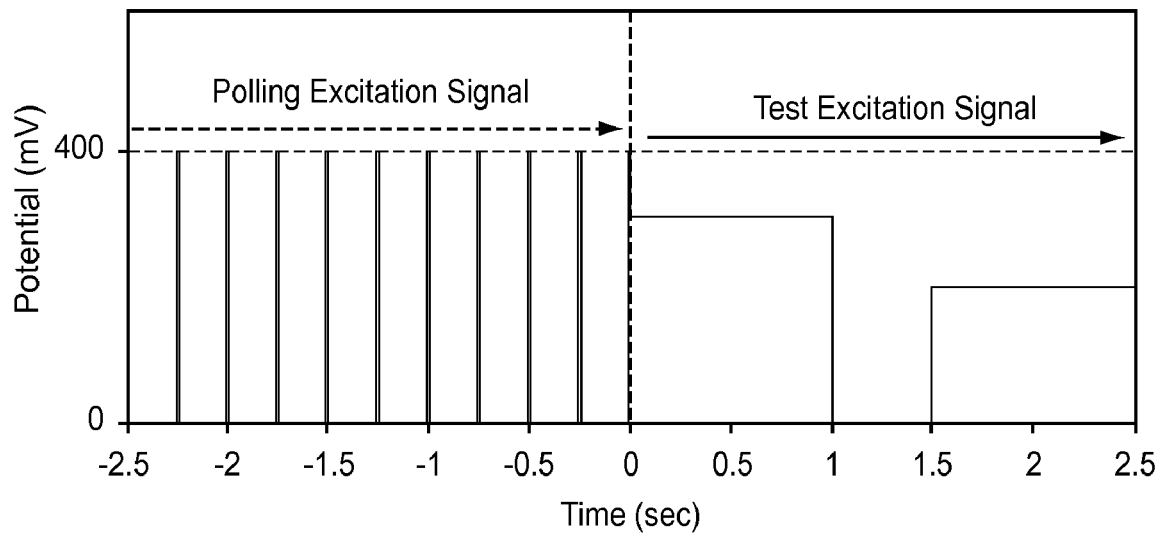
FIG. 4 is a graph illustrating a first amplitude reduction at the start of the first test pulse and a second amplitude reduction between the first and second pulses of the test excitation signal.
Figure 5:
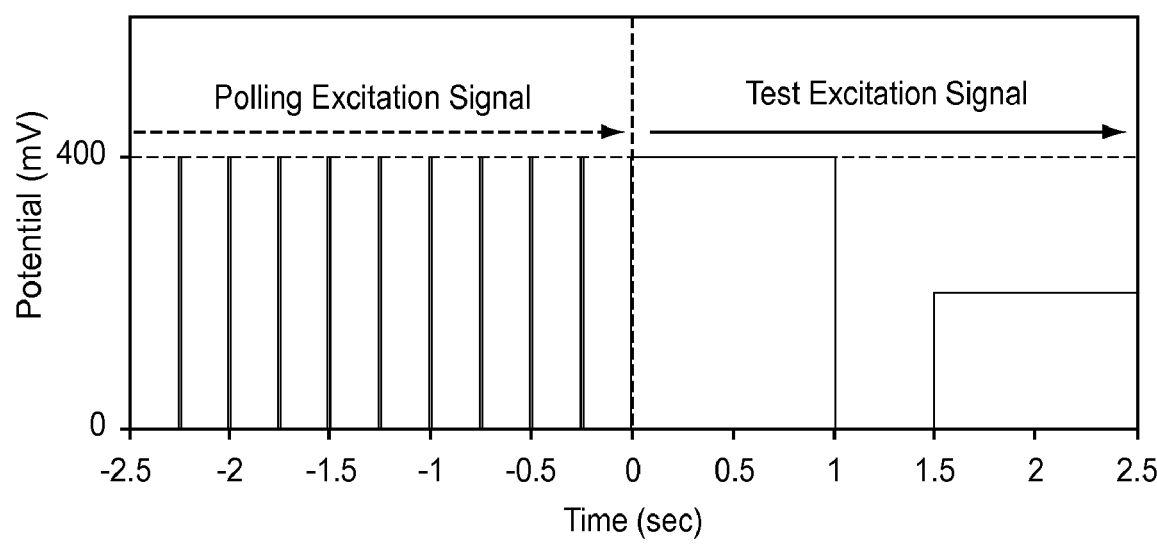
FIG. 5 is a graph illustrating an amplitude reduction between the first and second pulses of the test excitation signal.
Figure 6:
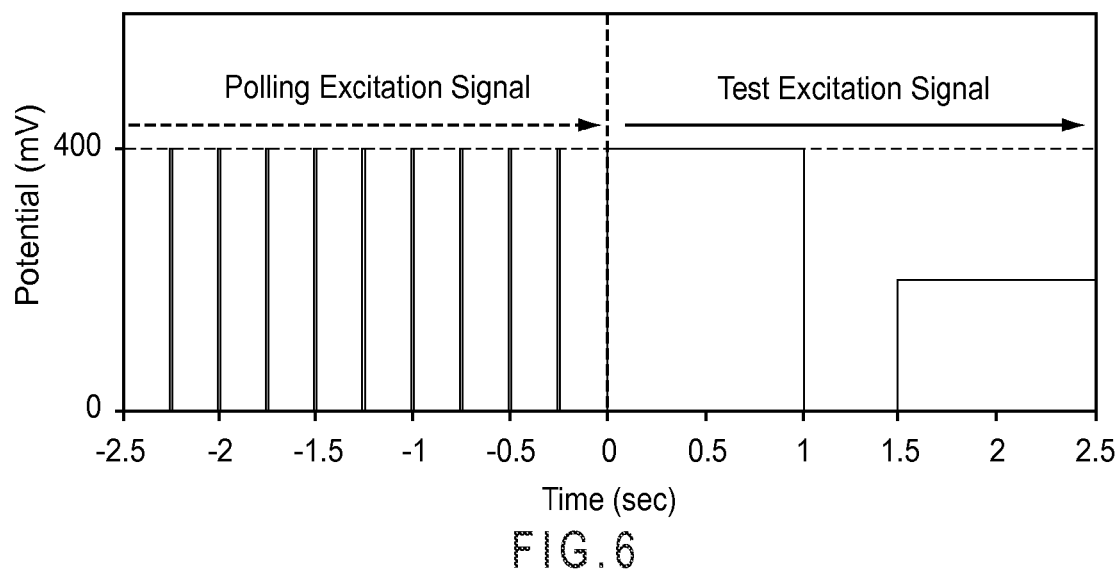
FIG. 6 is a graph illustrating another amplitude reduction between the first and second pulses of the test excitation signal.
Figure 7:
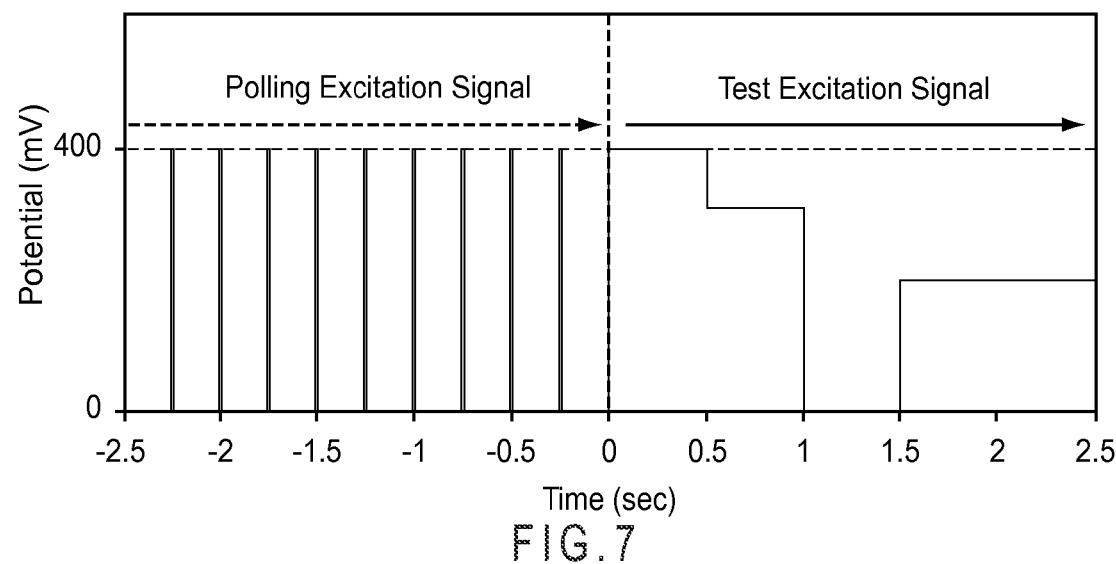
FIG. 7 is a graph illustrating a first amplitude reduction within the first test pulse and a second amplitude reduction between the first and second pulses of the test excitation signal.

FIGS. 3-7 are graphs illustrating the polling and test excitation signals for an underfill detection system. While a polling excitation signal is shown, the underfill detection system may operate without a polling excitation signal. In FIGS. 3-5, there is little or no polling relaxation width between the last polling pulse of the polling excitation signal and the first test pulse of the test excitation signal. In FIGS. 6-7, the polling relaxation width between the last polling pulse and the first test pulse may be the same or different than another polling relaxation width in the polling excitation signal.

In FIGS. 3-7, the polling excitation signal has an amplitude of about 400 mV. The test excitation signal has an amplitude that is reduced to about 200 mV. The polling excitation signal has a polling pulse width of about 5 ms and a polling pulse interval of about 250 ms. The test excitation signal has a test pulse width of about 1 sec and a test pulse interval of about 1.5 sec. The test excitation signal may be a portion of the assay excitation signal for an electrochemical sensor system, such as gated amperometry, gated voltammetry, or the like. Other polling and test excitation signals may be used.

FIG. 3 is a graph illustrating an amplitude reduction at the beginning of the test excitation signal. There is little or no polling relaxation width between the last polling pulse of the polling excitation signal and the first test pulse of the test excitation signal. The transition from about 400 mV to about 200 mV occurs at about 0 sec, when the biosensor switches from the polling excitation signal to the test excitation signal.

FIG. 4 is a graph illustrating a first amplitude reduction at the start of the first test pulse and a second amplitude reduction between the first and second pulses of the test excitation signal. There is little or no polling relaxation width between the last polling pulse of the polling excitation signal and the first test pulse of the test excitation signal. A first transition from about 400 mV to about 300 mV occurs at about 0 sec, when the biosensor switches from the polling excitation signal to the test excitation signal. A second transition from about 300 mV to about 200 mV occurs at about 1-1.5 sec, between the first and second pulses.

FIG. 5 is a graph illustrating an amplitude reduction of the test pulse between the first and second pulses of the test excitation signal. There is little or no polling relaxation width between the last polling pulse of the polling excitation signal and the first test pulse of the test excitation signal. The transition from about 400 mV to about 200 mV occurs at about 1-1.5 sec, between the first and second pulses.

FIG. 6 is a graph illustrating another amplitude reduction of the test pulse between the first and second pulses of the test excitation signal. The polling relaxation width between the last polling pulse and the first test pulse may be the same or different than another polling relaxation width in the polling excitation signal. The transition from about 400 mV to about 200 mV occurs at about 1-1.5 sec, between the first and second pulses.

FIG. 7 is a graph illustrating a first amplitude reduction within the first test pulse and a second amplitude reduction between the first and second pulses of the test excitation signal. The polling relaxation width between the last polling pulse and the first test pulse may be the same or different than another polling relaxation width in the polling excitation signal. The first amplitude reduction occurs at about 0.5 sec, when the biosensor switches the amplitude from about 400 mV to about 300 mV in the first pulse. The second amplitude reduction occurs at about 1-1.5 sec, when the biosensor switches the amplitude from about 300 mV to about 200 mV between the first and second pulses.

In 108 of FIG. 1, the biosensor measures the test output signal generated by the sample. The sample generates the test output signal in response to the test excitation signal. The biosensor may show the test output signal on a display and/or may store test output signal in a memory device.

Figure 8:
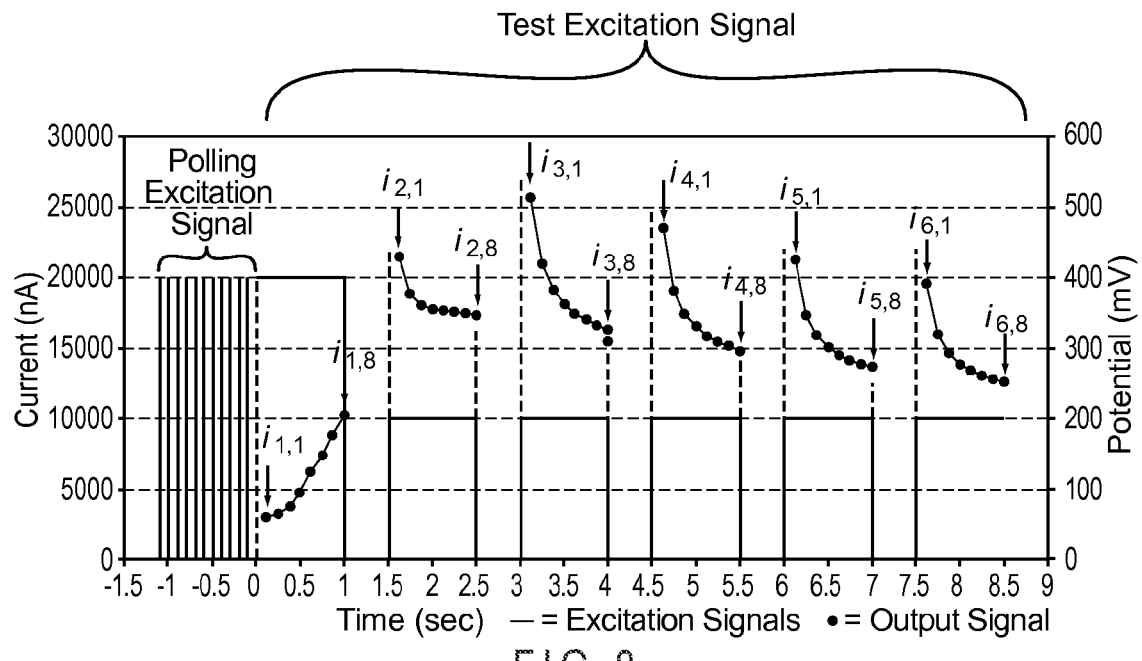
FIG. 8 is a graph illustrating the test output signal in relation to polling and test excitation signals.

FIG. 8 is a graph illustrating the test output signal in relation to polling and test excitation signals. The sample of biological fluid essentially fills the sample chamber; in other words, no underfill condition exists. When the sample chamber is essentially filled with the sample, the enzymatic and electrochemical reactions occur and the test output signal or current is generated in response to the test excitation signal or potential as expected. Other polling and test excitation signals may be used. Other test output signals may result including those that may decline initially and those that may decline in all pulses.

The polling excitation signal has an amplitude of about 400 mV with a polling pulse width of about 50 ms and a polling pulse interval of about 250 ms. The test excitation signal has an initial amplitude of 400 mV that is reduced to a final amplitude of about 200 mV. The test excitation signal has a test pulse width of about 1 sec and a test pulse interval of about 1.5 sec. The initial amplitude of the test excitation signal is reduced to the final amplitude between the first and second pulses. The transition from about 400 mV to about 200 mV occurs at about 1-1.5 sec. The test excitation signal may be a portion of the assay excitation signal for an electrochemical sensor system, such as gated amperometry, gated voltammetry, and the like.

The sample generates current or the test output signal in response to the applied potential or test excitation signal. The applied potential of the first test pulse is about 400 mV, which is essentially the same as the applied potential of the polling pulses. The current of the first test pulse increases from the beginning to the end of the pulse. The transition from a higher to lower potential occurs between the first and second test pulses. The applied potential of the second and following test pulses is about 200 mV. The current of the second and following test pulses is higher at the beginning of the test pulse than current at the end of the previous test pulse. The current of the second and following test pulses decreases from the beginning to the end of the pulse.

In FIG. 8, the test output signal and polling and test excitation signals may be for a biosensor having a working electrode, a counter electrode, and trigger electrode (which may be a sub-unit or sub-element of the counter electrode). The biosensor may measure the concentration of glucose in whole blood. Other biosensors may be used including those with additional electrodes and different configurations. Other analyte concentrations may be measured including those in other biological fluids.

In use, a sensor strip is inserted into the sensor port of the biosensor and the power is turned-on. The biosensor applies the polling excitation signal or polling potential to the working and counter electrodes of the sensor strip with the pulses having a pulse width of about 5-10 ms and a pulse interval of about 125 ms. The biosensor waits for application of the sample (whole blood) to the sensor strip. The biosensor measures the polling output signal. The biosensor may have a potentiostat that provides the polling output signal to the input of an analog comparator.

When there is only enough of the sample (whole blood) to cover the trigger electrode and the working electrode, there may be a short burst of current under a polling excitation signal of about 400 mV. When the output signal is equal to or greater than a polling threshold value, the biosensor applies the test excitation signal or potential to the working and counter electrodes. The polling threshold valve may be about 250 nA. The test excitation signal may be part of the assay excitation signal in an electrochemical sensor system. The test and assay excitation signals may be essentially the same signal. The comparator may compare the polling output signal to the polling threshold value. When the polling output signal exceeds the polling threshold value, the output signal of the comparator may trigger the launch of the test excitation signal.

During the test excitation signal, the biosensor may apply a first test pulse having a potential of about 400 mV for about 1 sec to the working and counter electrodes. The first test pulse is followed by a 0.5 sec test relaxation, which may be an essentially open circuit or the like. The test output signal or current within the first pulse is measured and stored in a memory device. The biosensor may apply a second pulse to the working and counter electrodes at about 200 mV for about 1 sec. This potential switch from about 400 mV to about 200 mV may trigger a negative current if there is an insufficient sample in the sensor strip, especially when the sample covers only the working and trigger electrodes. The test output signal or current within the second pulse is measured and stored in a memory device. The biosensor continues applying test pulses from the test excitation signal to the working and counter electrodes until the end of the test period or for as long as desired by the biosensor. The test period may be about 1 through about 10 sec. The test output signal or test current within each test pulse may be measured and stored.

The test output signals or test currents may be compared with one or more filters to detect whether an underfill condition exists. The filters may be underfill thresholds where the test output signals indicate there is not enough of the sample in the sensor strip. For a first filter, any one of the test currents within a test pulse may be compared with a first underfill threshold value to detect whether an underfill condition exists. For example, the current $i_{2,8}$ at the end of the second test pulse may be compared with a first underfill threshold of about 150 nA. For a second filter, the difference between the two test currents may be compared to a second threshold value to detect whether an underfill condition exists. For example, the difference between the last current in the first pulse $i_{1,8}$ and the first current in the second pulse $i_{2,1}$ may be compared to a second threshold value of about 700 nA. The filters may be used separately or in combination such as when the second filter detects an underfilled condition that the first filter did not detect. When one of the filtering conditions is met, the biosensor may provide an error signal or other indication to the user. The biosensor may stop applying the test excitation signal and prompt the user to add more blood to the sensor strip. The user may be able to recover from the underfill condition and avoid wasting a sensor strip.

FIGS. 9-12 are graphs illustrating the test output signals of underfilled and filled conditions. The underfilled conditions are for samples of about 1.2 micro-Liters (µL). The filled conditions are for samples of about 2.0 µL. The current profiles of the filled conditions are similar to the current profile illustrated in FIG. 6. The underfilled conditions generated test output signals or current profiles with a negative current that dropped below about −1100 nA within about 2.5 sec.

The test output signals or current profiles of the underfilled and filled conditions are responsive to polling and excitation signals or applied potentials. The polling excitation signal has an amplitude or potential of about 400 mV with a polling pulse width of about 5 ms and a polling pulse interval of about 62.5 ms. The test excitation signal has an amplitude that reduces to about 200 mV. The test excitation signal has a test pulse width of about 1 sec and a test pulse interval of about 1.5 sec. The polling excitation signal switches to the test excitation signal when the polling output signal is equal to or greater than a polling threshold. The polling threshold may be about 250 nA. Other polling thresholds may be used. The test excitation signal may be a portion of an assay excitation signal for an electrochemical sensor system, such as gated amperometry, gated voltammetry, or the like.

Figure 9:
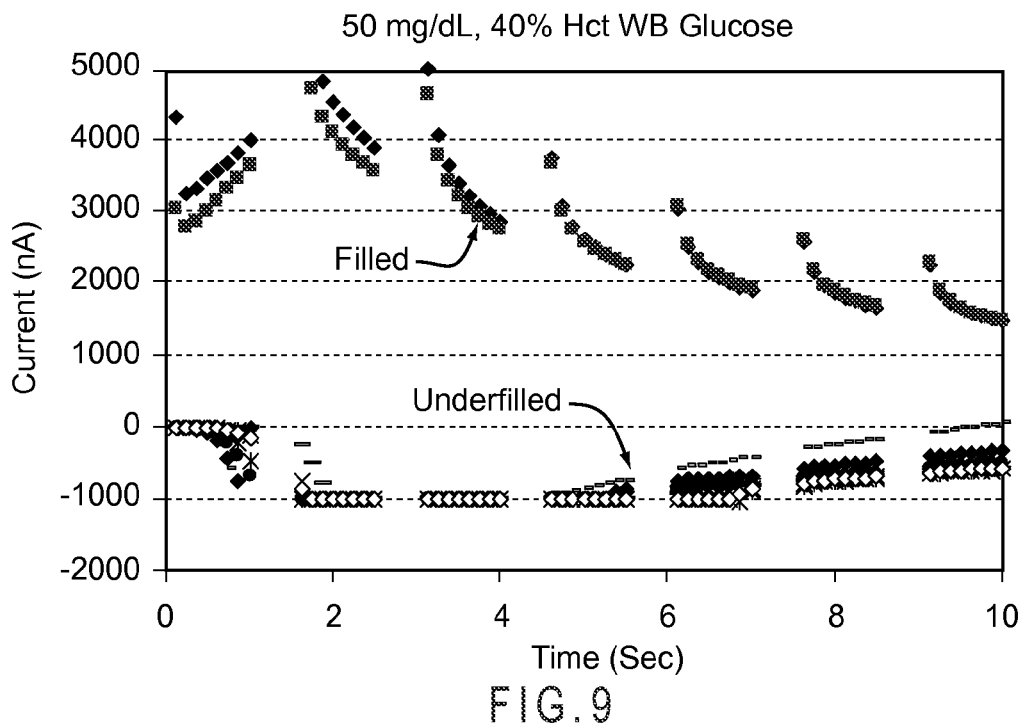
FIG. 9 is a graph illustrating the test output signals of underfilled and filled conditions when the amplitude is reduced at the beginning of the test excitation signal.

FIG. 9 is a graph illustrating the test output signals of underfilled and filled conditions when the amplitude is reduced at the beginning of the test excitation signal. The samples are whole blood having a glucose concentration of about 50 milligrams per deciliter (mg/dL) and about 40% hematocrit. The amplitude reduction occurs at about 0 sec, when the amplitude switches from about 400 mV to about 200 mV at the beginning of the first test pulse. The underfilled condition generated a test output signal with a negative current during the first pulse of the test excitation signal.

Figure 10:
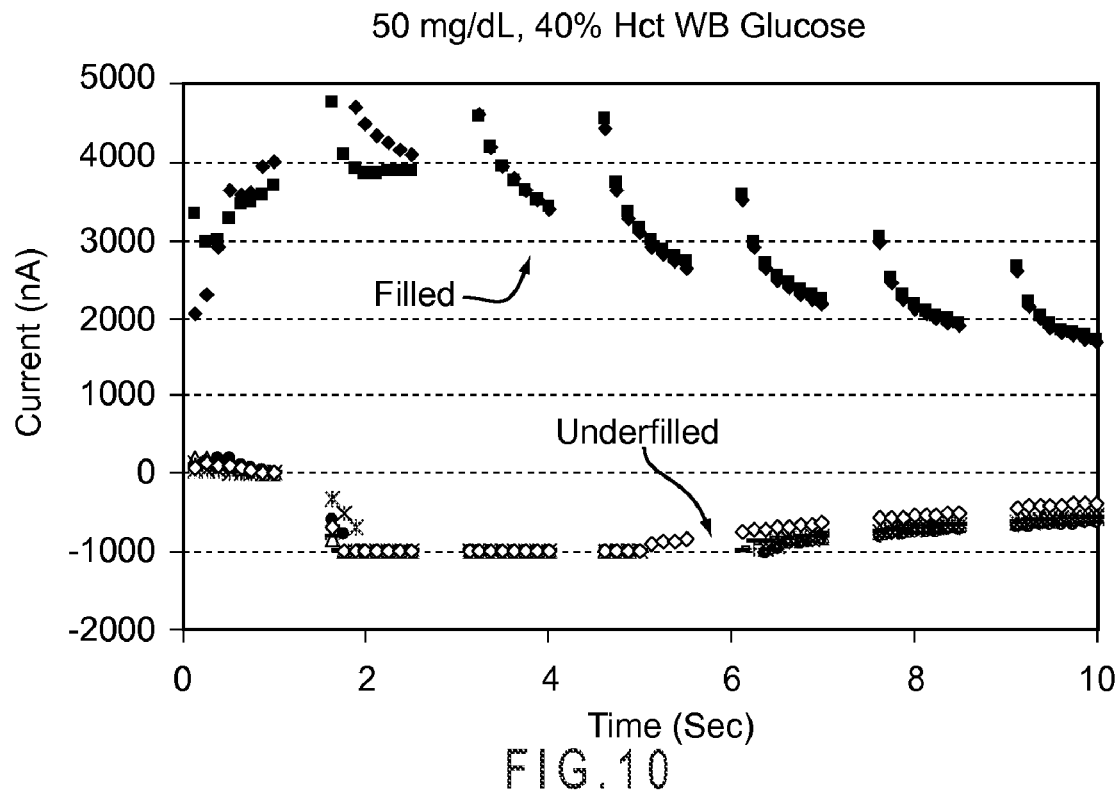
FIG. 10 is a graph illustrating the test output signals of underfilled and filled conditions when a first amplitude reduction occurs at the beginning of the first test pulse and a second amplitude reduction occurs between the first and second test pulses of the test excitation signal.

FIG. 10 is a graph illustrating the test output signals of underfilled and filled conditions when a first amplitude reduction occurs at the beginning of the first test pulse and a second amplitude reduction occurs between the first and second test pulses of the test excitation signal. The samples are whole blood having a glucose concentration of about 50 mg/dL and about 40% hematocrit. The first amplitude reduction occurs at about 0 sec, when the amplitude switches from about 400 mV to about 300 mV at the beginning of the first test pulse. The second amplitude reduction occurs at about 1-1.5 sec, when the amplitude switches from about 300 mV to about 200 mV between the first and second pulses. The underfilled condition generated a test output signal with a current close to zero during the first pulse of the test excitation signal; when the test pulse was reduced from about 400 mV to about 300 mV. The underfilled condition generated a test output signal with a negative current during the second pulse of the test excitation signal; after the test pulse was reduced from about 300 mV to about 200 mV.

Figure 11:
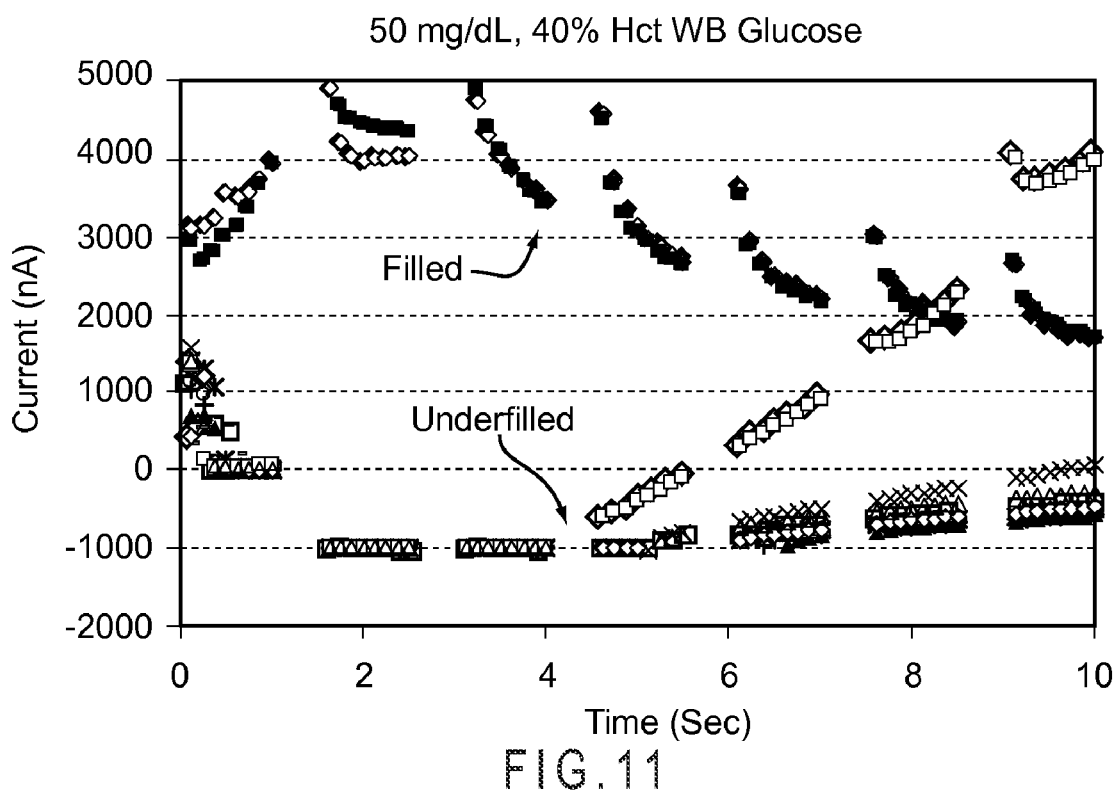
FIG. 11 is a graph illustrating the test output signals of underfilled and filled conditions when the amplitude of the test pulse is reduced between the first and second pulses.

FIG. 11 is a graph illustrating the test output signals of underfilled and filled conditions when the amplitude is reduced between the first and second test pulses of the test excitation signal. The samples are whole blood having a glucose concentration of about 50 mg/dL and about 40% hematocrit. The amplitude reduction occurs at about 1-1.5 sec; when the amplitude switches from about 400 mV to about 200 mV between the first and second test pulses. The underfilled condition generated a test output signal with a positive current during the first pulse of the test excitation signal; when the applied potential of the test pulse remained essentially the same as the applied potential of the polling pulse. The underfilled condition generated a test output signal with a negative current during the second pulse of the test excitation signal; after the test pulse was reduced from about 400 mV to about 200 mV.

Figure 12:
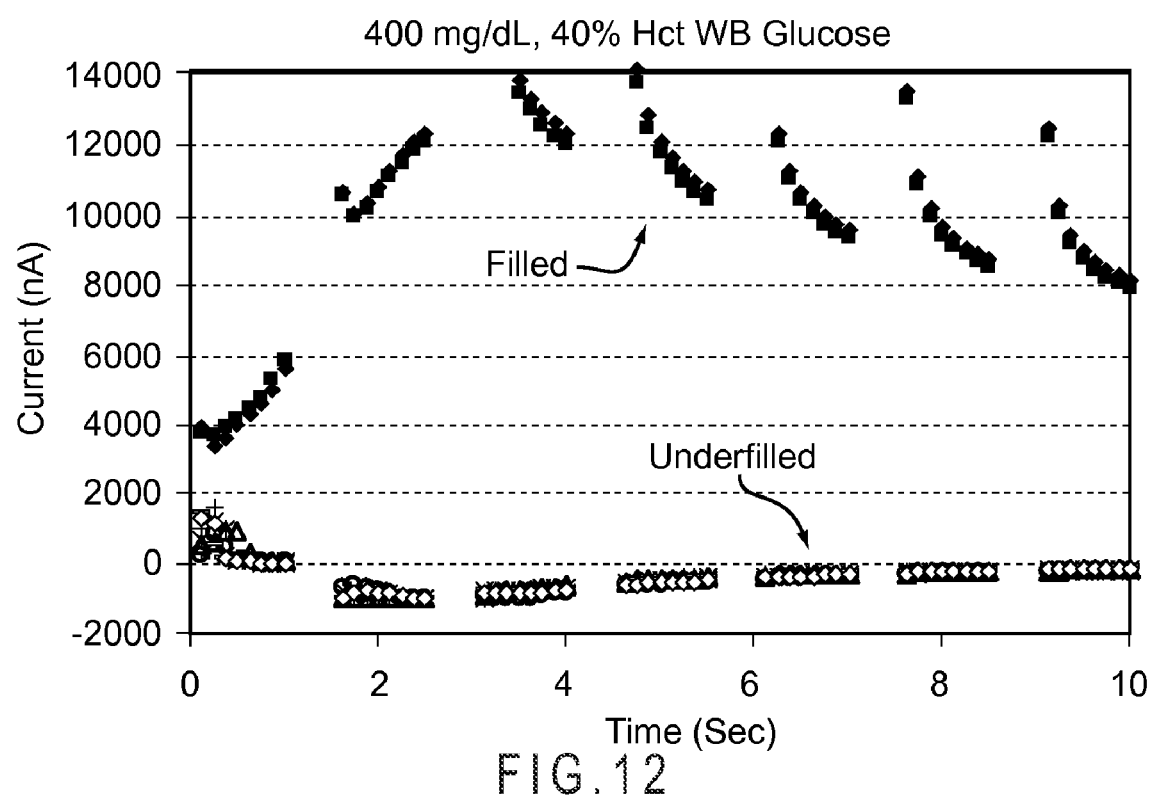
FIG. 12 is a graph illustrating other test output signals of underfilled and filled conditions when the amplitude of the test pulse is reduced between the first and second pulses.

FIG. 12 is a graph illustrating the test output signals of underfilled and filled conditions when the amplitude of the test pulse is reduced between the first and second pulses. The samples are whole blood having a glucose concentration of about 400 mg/dL and about 40% hematocrit. The amplitude reduction occurs at about 1-1.5 sec, when the amplitude switches from about 400 mV to about 200 mV. During the first pulse of the test excitation signal, the applied potential of the test pulse remained essentially the same as the applied potential of the polling pulse. The underfilled condition generated a test output signal with a positive current during the first pulse. The underfilled condition generated a test output signal with a negative current during the second pulse of the test excitation signal; after the test pulse was reduced from about 400 mV to about 200 mV.

In 110 of FIG. 1, the biosensor compares the test output signal with one or more underfill thresholds during the test period. The underfill thresholds may be predetermined threshold values stored in a memory device, obtained from a lookup table, or the like. The predetermined threshold values may have been developed from a statistical analysis of laboratory work. Other predetermined threshold values may be used. The underfill thresholds may be measured or calculated threshold values in response to the test output signal. Other measured or calculated threshold values may be used.

The underfill thresholds may be selected to identify when a test output signal is stronger or weaker in response to an underfill condition. The underfill thresholds may be selected to identify weaker test output signals generated in response to a switch from a higher to lower amplitude in a test excitation signal. The underfill thresholds may be selected to identify negative test output signals generated in response to a switch from a higher to lower amplitude in a test excitation signal. The underfill thresholds may be selected to identify stronger test output signals generated in response to a switch from a lower to higher amplitude in a test excitation signal. The underfill thresholds may be selected to identify when a change in a test output signal is responsive to an underfill condition. Other underfill thresholds may be used.

The test output signal may indicate an underfill condition when the test output signal is equal to or less than a first underfill threshold. The first underfill threshold may be predetermined threshold value stored in a memory device, obtained from a lookup table, or the like. The first underfill threshold may be a measured or calculated threshold value in response to the test output signal. The first underfill threshold may be less than about 50% or 75% of the expected or measured test output signal at the beginning of the first test pulse. The first underfill threshold may be less than about 10% of the expected or measured test output signal at the beginning of the first test pulse. The first underfill threshold may be in the range of about 2% through about 8% of the expected or measured test output signal at the beginning of the first test pulse. The first underfill threshold may be in the range of about 5% of the expected or measured test output signal at the beginning of the first test pulse. The first underfill threshold may be about zero. For example, the first underfill threshold for the test output signals of FIGS. 9-12 may be in the range of about 100 nA through about 200 nA. Other first underfill thresholds may be used.

The test output signal may indicate an underfill condition when a change in the test output signal is equal to or greater than a second underfill threshold. The change may be a decrease in the test output signal generated in response to a switch from a higher to lower amplitude in a test excitation signal. The change may be an increase in the test output signal generated in response to a switch from a lower to higher amplitude in a test excitation signal. The second underfill threshold may be predetermined threshold value stored in a memory device, obtained from a lookup table, or the like. The second underfill threshold may be a measured or calculated threshold value in response to the test output signal. The second underfill threshold may be greater than about 5% or 100% of the expected or measured test output signal at the beginning of the first test pulse. The second underfill threshold may be in the range of about 5% through about 90% of the expected or measured test output signal at the beginning of the first test pulse. The second underfill threshold may be in the range of about 25% through about 75% of the expected or measured test output signal at the beginning of the first test pulse. The second underfill threshold may be about 50% of the expected or measured test output signal at the beginning of the first test pulse. For example, the second underfill threshold for the test output signals of FIGS. 9-12 may be in the range of about 500 nA through about 2000 nA. Other second underfill thresholds may be used.

The test output signal may indicate an underfill condition when the test output signal is equal to or greater than a third underfill threshold. The third underfill threshold may be predetermined threshold value stored in a memory device, obtained from a lookup table, or the like. The third underfill threshold may be a measured or calculated threshold value in response to the test output signal. The third underfill threshold may be greater than about 150% or 200% of the expected or measured test output signal at the beginning of the first test pulse. The third underfill threshold may be greater than about 110% of the expected or measured test output signal at the beginning of the first test pulse. The third underfill threshold may be in the range of about 102% through about 108% of the expected or measured test output signal at the beginning of the first test pulse. The third underfill threshold may about 105% of the expected or measured test output signal at the beginning of the first test pulse. Other third underfill thresholds may be used.

Figure 13:
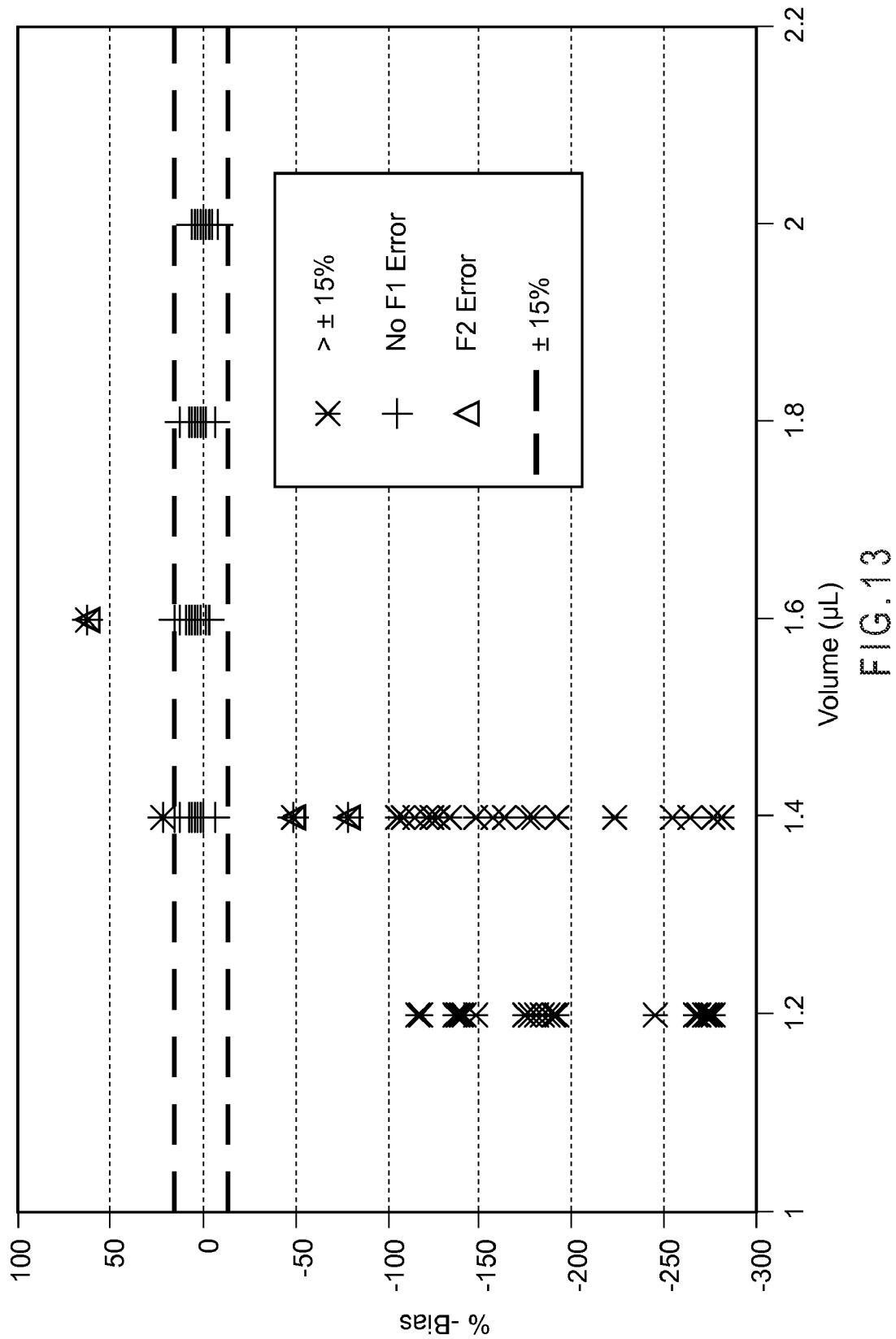
FIG. 13 is a graph illustrating the percent bias of analyte analyses in relation to the volume of a sample.

FIG. 13 is a graph illustrating the percent bias of analyte analyses in relation to the volume of a sample. The analyte analyses determined the concentration of glucose in samples of whole blood. The percent of bias (%-bias) is an error measurement of the relative difference between the glucose concentration determined by each analysis and the glucose concentration of the sample when sufficiently filled. The sample volumes were in a range of about 1.2 µL through about 2.0 µL. A sufficiently filled sample volume was about 2.0 µL.

The test output signals from the analyte analysis were screened by two filters (Filter 1 and Filter 2) to identify samples with underfill conditions. A Filter 1 (F1) error indicates the sample has an underfill condition when the test output signal is equal to or less than a first underfill threshold. A Filter 2 (F2) error indicates the sample has an underfill condition when a decrease in the test output signal at or after the transition from a higher to lower test pulse is equal to or greater than a second underfill threshold. Other filters may be used.

There were three types of test output signals from the analyses in FIG. 13: (1) test output signals indicating no F1 errors; (2) test output signals indicating a F1 error; and (3) test output signals indicating no F1 error, but indicating a F2 error. Of the test output signals indicating no F1 errors, only four analyses had a %-bias greater than about ±15%. Three of the analyses with a %-bias greater than about ±15% and not detected as F1 errors were detected as F2 errors.

Figure 14:
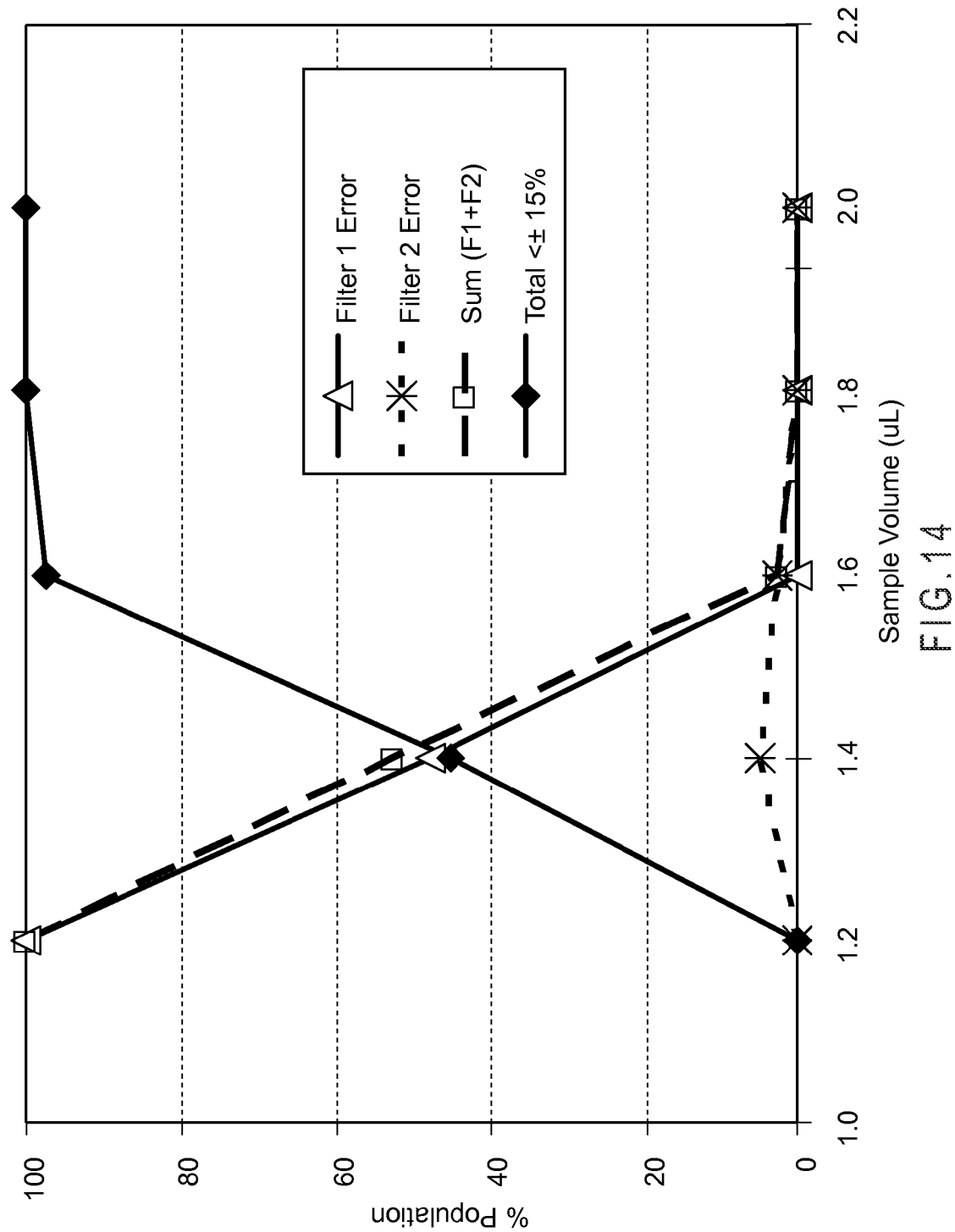
FIG. 14 is a graph illustrating the percent population of different types of test output signals in relation to the volume of a sample for the analyte analyses of FIG. 11.

FIG. 14 is a graph illustrating the percent population of different types of test output signals in relation to the volume of a sample for the analyte analyses of FIG. 13. The percent population (%-population) is the proportion of the analyte analyses having a particular type of test output signal at a sample volume. The analyte analyses with test output signals having F1 or F2 errors were essentially exclusive from the analyte analyses with a %-bias less than ±15%. Essentially, those analyte analyses with test output signals not screened out by F1 or F2 errors had a %-bias less than ±15%. The detection rate was greater than about 98% for underfill conditions of analyses with a %-bias greater than about ±15%. The detection rate was greater than about 90% for underfill conditions of analyses with a %-bias greater than about ±10%. The detection rates may be further refined with different threshold values. Factors other than underfill may contribute to %-bias greater than ±15%.

In 112 of FIG. 1, the biosensor generates an error signal or other indication in response to an underfill condition when the test output signal indicates the sample size is not large enough. The error signal may be shown on a display device and/or retained in a memory device. The biosensor may provide the error signal during or after the analysis of one or more analytes in the sample is performed. The biosensor may provide the error signal immediately after detection and/or prior to the analysis of the analyte. The error signal may request the addition of biological fluid to the sample prior to proceeding with the analysis of the analyte. The error signal may stop the analysis of the analyte. Stop includes not starting or suspending the analysis.

Figure 15:
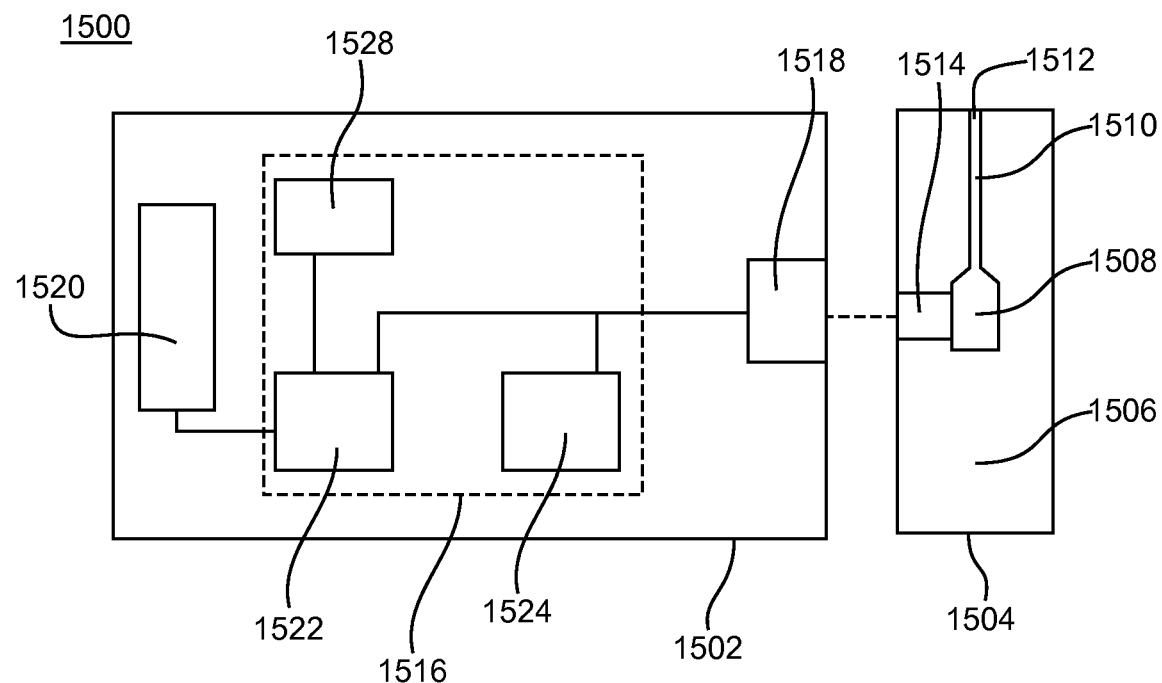
FIG. 15 depicts a schematic representation of a biosensor with an underfill detection system.

FIG. 15 depicts a schematic representation of a biosensor 1500 with an underfill detection system. Biosensor 1500 determines an analyte concentration in a sample of a biological fluid. The underfill detection system indicates when a sample of the biological fluid is not large enough to provide an accurate and/or precise analysis of one or more analytes as previously discussed. Biosensor 1500 includes a measuring device 1502 and a sensor strip 1504, which may be implemented as a bench-top device, a portable or hand-held device, or the like. The measuring device 1502 and sensor strip 1504 may be adapted to implement an electrochemical sensor system, an optical sensor system, a combination thereof, or the like. The underfill detection system may improve the accuracy and/or precision of the biosensor 1500 in determining when underfill conditions occur. Biosensor 1500 may be utilized to determine one or more analyte concentrations, such as glucose, uric acid, lactate, cholesterol, bilirubin, or the like, in a biological fluid, such as whole blood, urine, saliva, or the like. While a particular configuration is shown, biosensor 1500 may have other configurations, including those with additional components.

The sensor strip 1504 has a base 1506 that forms a reservoir 1508 and a channel 1510 with an opening 1512. The reservoir 1508 and channel 1510 may be covered by a lid with a vent. The reservoir 1508 defines a partially-enclosed volume (the cap-gap). The reservoir 1508 may contain a composition that assists in retaining a liquid sample such as water-swellable polymers or porous polymer matrices. Reagents may be deposited in the reservoir 1508 and/or channel 1510. The reagents may include one or more enzymes, mediators, binders, and other active or non-reactive species. The reagents may include a chemical indicator for an optical system. The sensor strip 1504 also may have a sample interface 1514 disposed adjacent to the reservoir 1508. The sample interface 1514 may partially or completely surround the reservoir 1508. The sensor strip 1504 may have other configurations.

The sample interface 1514 has conductors connected to a working electrode and a counter electrode. The electrodes may be substantially in the same plane. The electrodes may be separated by greater than 200 or 250 µm and may be separated from the lid by at least 100 µm. The electrodes may be disposed on a surface of the base 1506 that forms the reservoir 1508. The electrodes may extend or project into the cap-gap formed by the reservoir 1508. A dielectric layer may partially cover the conductors and/or the electrodes. The counter electrode may have a sub-element or trigger electrode. The sub-element may be located upstream from the working electrode. The trigger electrode may be a third electrode. The sample interface 1514 may have other electrodes and conductors. The sample interface 1514 may have one or more optical portals or apertures for viewing the sample. The sample interface 1514 may have other components and configurations.

The measuring device 1502 includes electrical circuitry 1516 connected to a sensor interface 1518 and a display 1520. The electrical circuitry 1516 includes a processor 1522 connected to a signal generator 1524, and a storage medium 1528. The measuring device may have other components and configurations.

The signal generator 1524 provides electrical input signals to the sensor interface 1518 in response to the processor 1522. The electrical input signals may include the polling and test excitation signals used in the underfill detection system. The electrical input signals may include electrical signals used to operate or control a detector and light source in the sensor interface 1518 for an optical sensor system. The electrical input signals may include an assay excitation signal used in an electrochemical sensor system. The polling and test excitation signals for the underfill detection system may be part of or incorporated with the assay excitation signal for an electrochemical sensor system. The electrical input signals may be transmitted by the sensor interface 1518 to the sample interface 1514. The electrical input signals may be a potential or current and may be constant, variable, or a combination thereof, such as when an AC signal is applied with a DC signal offset. The electrical input signals may be applied as a single pulse or in multiple pulses, sequences, or cycles. The signal generator 1524 also may record signals received from the sensor interface 1518 as a generator-recorder.

The storage medium 1528 may be a magnetic, optical, or semiconductor memory, another computer readable storage device, or the like. The storage medium 1528 may be a fixed memory device or a removable memory device such as a memory card.

The processor 1522 implements the underfill detection, analyte analysis, and data treatment using computer readable software code and data stored in the storage medium 1528. The processor 1522 may start the underfill detection and analyte analysis in response to the presence of sensor strip 1504 at the sensor interface 1518, the application of a sample to the sensor strip 1504, user input, or the like. The processor 1522 directs the signal generator 1524 to provide the electrical input signals to the sensor interface 1518.

The processor 1522 receives and measures output signals from the sensor interface 1518. The output signals may be electrical signals, such as current or potential, or light. The output signals may include the polling and test output signals used in the underfill detection system. The output signals may include an assay output signal generated in response to the redox reaction of the analyte in the sample. The output signal may be generated using an optical system, an electrochemical system, or the like. The test output signal for the underfill detection system may be part of or incorporated with the assay output signal for an electrochemical sensor system. The processor 1522 may compare the polling output signals to one or more polling thresholds as previously discussed. The processor 1522 may compare the test output signals to one or more underfill thresholds as previously discussed.

The processor 1522 provides an error signal or other indication of an underfill condition when the test output signal indicates the sample size is not large enough. The processor 1522 may display the error signal on the display 1520 and may store the error signal and related data in the storage medium 1528. The processor 1522 may provide the error signal at any time during or after the analyte analysis. The processor 1522 may provide the error signal when an underfill condition is detected and may prompt a user to add more of the biological fluid to the sensor strip 1204. The processor 1522 may not proceed with the analyte analysis when an underfill condition is detected.

The processor 1522 determines analyte concentrations from the assay output signals. The results of the analyte analysis are output to the display 1520 and may be stored in the storage medium 1528. Instructions regarding implementation of the analyte analysis may be provided by the computer readable software code stored in the storage medium 1528. The code may be object code or any other code describing or controlling the described functionality. The data from the analyte analysis may be subjected to one or more data treatments, including the determination of decay rates, K constants, slopes, intercepts, and/or sample temperature in the processor 1522.

The sensor interface 1518 has contacts that connect or electrically communicate with the conductors in the sample interface 1514 of the sensor strip 1504. The sensor interface 1518 transmits the electrical input signals from the signal generator 1524 through the contacts to the connectors in the sample interface 1514. The sensor interface 1518 also transmits the output signals from the sample interface 1514 to the processor 1522 and/or signal generator 1524. The sensor interface 1508 also may include a detector, a light source, and other components used in an optical sensor system.

The display 1520 may be analog or digital. The display may be an LCD display adapted to displaying a numerical reading. Other displays may be used.

In use, a liquid sample of a biological fluid is transferred into the cap-gap formed by the reservoir 1508 by introducing the liquid to the opening 1512. The liquid sample flows through channel 1510 into reservoir 1508, filling the cap-gap while expelling the previously contained air. The liquid sample chemically reacts with the reagents deposited in the channel 1510 and/or reservoir 1508.

The processor 1522 detects when the sample of the biological fluid is available for analysis. The sensor strip 1502 is disposed adjacent to the measuring device 1502. Adjacent includes positions where the sample interface 1514 is in electrical and/or optical communication with the sensor interface 1508. Electrical communication includes the transfer of input and/or output signals between contacts in the sensor interface 1518 and conductors in the sample interface 1514. Optical communication includes the transfer of light between an optical portal in the sample interface 1502 and a detector in the sensor interface 1508. Optical communication also includes the transfer of light between an optical portal in the sample interface 1502 and a light source in the sensor interface 1508.

The processor 1522 may direct the signal generator 1524 to provide a polling excitation signal to sensor interface 1518, which applies the polling excitation signal to the sample through the electrodes in the sample interface 1514. The sample generates the polling output signal in response to the polling excitation signal. The sample interface 1514 provides the polling output signal to the sensor interface 1518. The processor 1522 receives the polling output signal from the sensor interface 1518. The processor 1522 may show the polling output signal on the display 1520 and/or may store the polling output signal in the storage medium 1528.

The processor 1522 may direct the signal generator 1524 to provide the test excitation signal to the sensor interface 1518 when the polling output signal is equal to or greater than a polling threshold. The processor 1522 may have comparator circuitry to provide the test excitation signal to the sensor interface 1518 when the polling output signal is equal to or greater than a polling threshold. In the comparator circuitry, the polling output signal is directed into the input of an electrical (analog) comparator or the like. The comparator compares the polling output signal with a polling threshold value. When the polling output signal is equal to or greater than the polling threshold value, the output of the comparator triggers the launch of the test excitation signal. When switching from the polling excitation signal to the test excitation signal, the processor 1522 may change the amplitude of the test pulses to a different amplitude than the amplitude of the polling pulses as previously discussed. The amplitude of the test pulses may be larger and/or smaller than the amplitude of the polling pulses. The amplitude of one test pulse may be larger or smaller than the amplitude of another test pulse. The processor 1522 may change the amplitude of the test pulses at or near the start of the test excitation signal and/or during a transition from one pulse to another. The processor 1522 may change the amplitude of the test pulses multiple times.

The sensor interface 1518 applies the test excitation signal to the sample through the sample interface 1514 during a test period. The sample generates the test output signal in response to the test excitation signal. The sample interface 1514 provides the test output signal to the sensor interface 1518.

The processor 1522 receives the test output signal from the sensor interface 1518. The processor 1522 measures the test output signal generated by the sample. The processor 1522 may show the test output signal on the display 1520 and/or may store test output signal in the storage medium 1528.

The processor 1522 compares the test output signal with one or more underfill thresholds during the test period as previously discussed. The test output signal may indicate an underfill condition when the test output signal is equal to or less than a first underfill threshold. The test output signal may indicate an underfill condition when a change in the test output signal is equal to or greater than a second underfill threshold. The test output signal may indicate an underfill condition when the test output signal is equal to or greater than a third underfill threshold.

The processor 1522 provides an error signal of an underfill condition when the test output signal indicates the sample size is not large enough. The error signal may be shown on the display 1520 and/or retained in the storage medium 1528. The processor 1522 may provide the error signal immediately or another time, such as after the analyte analysis. The processor 1522 may prompt a user to add more biological fluid to the sample prior to proceeding with the analysis of the analyte.

The processor 1522 directs the signal generator 1524 to provide the other electrical input signals to the sensor interface 1518. In an optical system, the sensor interface 1518 provides the electrical input signals to operate the detector and light source. The sensor interface 1518 receives the assay output signal from the detector. In an electrochemical system, the sensor interface 1518 applies the assay excitation signal to the sample through the sample interface 1514. The test excitation signal for the underfill detection system may be part of or incorporated with the assay excitation signal. The sample generates the assay output signal from the redox reaction of the analyte in response to the assay excitation signal. The sample interface 1514 provides the assay output signal to the sensor interface 1518.

The processor 1522 receives the assay output signal from the sensor interface 1518. The processor 1522 determines the analyte concentration of the sample in response to the assay output signal. The processor 1522 may show the assay output signal on the display 1520 and/or may store the assay output signal in the storage medium 1528.

Without limiting the scope, application, or implementation, the methods and systems previously described may be implemented using an algorithm, such as the following:

| Step 1: | Turn on biosensor power |
|---|---|
| Step 2: | Perform biosensor self-test |
| Step 3: | Setup to poll for application of sample to sensor |
| Step 4: | Setup for testing the sensor current |
| Step 5: | Test if the sensor current exceeds the polling threshold |
| Step 6: | Delay and test sensor current again |
| Step 7: | Upon detection of Sample Application start counting time launch pulse sequence |
| Step 8: | Pulse 1 - Measure sensor currents $i_{1.1}$ and $i_{1.8}$ |
| Step 9: | Pulse 2 - Measure sensor currents $i_{2.1}$ and $i_{2.8}$ |
| Step 10: | Delay 2 - |
| Step 11: | Pulse 3 - Measure sensor currents: $i_{3.1}$ and $i_{3.8}$ |
| Step 12: | Delay 3 - |
| Step 13: | Pulse 4 - Measure sensor currents: $i_{4.1}$, $i_{4.4}$, and $i_{4.8}$ |
| Step 14: | Delay 4 - |
| Step 15: | Pulse 5 - Measure sensor currents: $i_{5.1}$, $i_{5.4}$, and $i_{5.8}$ |
| Step 16: | Look up slope and intercept for lot calibration number S = Slope value for current lot calibration number Int = Intercept value for current lot calibration number |
| Step 17: | Adjust slope and intercept for temperature effect |
| Step 18: | Calculate glucose concentration at 25° C. |
| Step 19: | Convert to target reference (plasma vs. WB reference) |
| Step 20: | Check underfill If ($i_{2.8}$ < $Underfill_{Min}$) or (($i_{1.8}$-$i_{2.1}$) > $Underfill_{Delta}$) then BEGIN If (ErrorCode is not set) then set ErrorCode to "Underfill" END |
| Step 21: | Convert to correct units of measure setting |
| Step 22: | Display result |

One example of the constants that may be used in the algorithm is given in Table I below. Other constants may be used.

TABLE I

| Constant | Description | Value | Units |
|---|---|---|---|
| $Underfill_{Min}$ | current threshold for underfill check, $1^{st}$ criteria | 150 | nA |
| $Underfill_{Delta}$ | current delta threshold for underfill, $2^{nd}$ criteria | 700 | nA |

To provide a clear and more consistent understanding of the specification and claims of this application, the following definitions are provided.

"Analyte" is defined as one or more substances present in a sample. An analysis determines the presence and/or concentration of the analyte present in the sample.

"Sample" is defined as a composition that may contain an unknown amount of the analyte. Typically, a sample for electrochemical analysis is in liquid form, and preferably the sample is an aqueous mixture. A sample may be a biological sample, such as blood, urine, or saliva. A sample also may be a derivative of a biological sample, such as an extract, a dilution, a filtrate, or a reconstituted precipitate.

"Conductor" is defined as an electrically conductive substance that remains stationary during an electrochemical analysis.

"Accuracy" is defined as how close the amount of analyte measured by a sensor system corresponds to the true amount of analyte in the sample. Accuracy may be expressed in terms of the bias of the sensor system's analyte reading in comparison to a reference analyte reading. Larger bias values reflect less accuracy.

"Precision" is defined as how close multiple analyte measurements are for the same sample. Precision may be expressed in terms of the spread or variance among multiple measurements.

"Redox reaction" is defined as a chemical reaction between two species involving the transfer of at least one electron from a first species to a second species. Thus, a redox reaction includes an oxidation and a reduction. The oxidation half-cell of the reaction involves the loss of at least one electron by the first species, while the reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained.

"Mediator" is defined as a substance that may be oxidized or reduced and that may transfer one or more electrons. A mediator is a reagent in an electrochemical analysis and is not the analyte of interest, but provides for the indirect measurement of the analyte. In a simple system, the mediator undergoes a redox reaction in response to the oxidation or reduction of the analyte. The oxidized or reduced mediator then undergoes the opposite reaction at the working electrode of the sensor strip and is regenerated to its original oxidation number.

"Binder" is defined as a material that provides physical support and containment to the reagents while having chemical compatibility with the reagents.

"Underfill condition" is defined as a sample of biological fluid in a biosensor having a size or volume that is not large enough for the biosensor to accurately and/or precisely analyze the concentration of one or more analytes in the biological fluid.

"Handheld device" is defined as a device that may be held in a human hand and is portable. An example of a handheld device is the measuring device accompanying Ascensia® Elite Blood Glucose Monitoring System, available from Bayer HealthCare, LLC, Elkhart, Ind.

While various embodiments of the invention have been described, it will be apparent to those of ordinary skill in the art that other embodiments and implementations are possible within the scope of the invention.

What is claimed is:

1. A method for detecting an underfill condition in a biosensor, comprising:
    applying a test excitation signal to a sample of a biological fluid;
    switching the test excitation signal to at least one different amplitude;
    measuring a test output signal responsive to a redox reaction of the sample;
    comparing the test output signal with at least one underfill threshold; and
    detecting an underfill condition in the biosensor from the comparison of the test output signal with the at least one underfill threshold.

2. The method of claim 1, where the test excitation signal has a test pulse width of less than about 5 sec, and where the test excitation signal has a test pulse interval of less than about 15 sec.

3. The method of claim 1, where the at least one different amplitude is lower than an original amplitude.

4. The method of claim 3, where the original and different amplitudes are selected from an output signal plateau in an electrochemical sensor system.

5. The method of claim 4, where the output signal plateau includes excitation amplitudes that generate output signals within ±5% of an average output signal.

6. The method of claim 1, further comprising switching the test excitation signal to at least one different amplitude essentially during at least one of a start of the test excitation signal, a test pulse, and a transition from one test pulse to another test pulse.

7. The method of claim 1, further comprising:
    switching the test excitation signal to a first different amplitude during a test pulse; and
    switching the test excitation signal to a second different amplitude during a transition from one test pulse to another test pulse.

8. The method of claim 1, further comprising decreasing the amplitude essentially during at least one of a start of the test excitation signal and transition from one test pulse to another test pulse.

9. The method of claim 1, further comprising decreasing the amplitude the test excitation signal multiple times.

10. The method of claim 1, further comprising generating an error signal in response to an underfill condition.

11. The method of claim 10, further comprising at least one of requesting the addition of biological fluid to the sample in response to the error signal and stopping an analysis of an analyte in the sample in response to the error signal.

12. The method of claim 1, further comprising applying a polling excitation signal to the sample, and switching the test excitation signal to a different amplitude than the polling excitation signal.

13. The method of claim 12, further comprising:
    generating a polling output signal in response to the polling excitation signal; and
    applying the test excitation signal to the sample when the polling output signal is equal to or greater than a polling threshold.

14. The method of claim 1, where the test excitation signal is part of an assay excitation signal in an electrochemical sensor system.

15. The method of claim 1, further comprising determining if any one test output signal current is equal to or less than the at least one underfill threshold.

16. The method of claim 15, further comprising determining if any one test output signal current is equal to or greater than a second underfill threshold.

17. The method of claim 15, where the text excitation signal includes at least first and second test pulses separated by a test relaxation, the method further comprising:
    comparing a difference between a test output signal current of the first test pulse and a test output signal current of the second test pulse with a second underfill threshold.

18. A method for detecting an underfill condition in a biosensor, comprising:
    applying a polling excitation signal to a sample of a biological fluid;
    applying a test excitation signal to the sample when a polling output signal from the sample is equal to or greater than a polling threshold;
    switching the test excitation signal to at least one different amplitude;
    measuring a test output signal from the sample;
    comparing the test output signal with at least one underfill threshold; and
    generating an error signal.

19. A biosensor for determining an analyte concentration in a biological fluid, comprising:

a sensor strip having a sample interface on a base, where the sample interface is adjacent to a reservoir formed by the base;

a measuring device having a processor connected to a sensor interface, where the sensor interface has electrical communication with the sample interface; and where the processor applies a test excitation signal to the sample interface, where the processor switches the test excitation signal to at least one different amplitude, where the processor measures a test output signal responsive to a redox reaction of the sample from the sample interface, and where the processor compares the test output signal to at least one underfill threshold to determine if the sensor strip is underfilled.

20. The biosensor of claim 19, where the processor applies a polling excitation signal to the sample.

21. The biosensor of claim 20, where the processor switches from the polling excitation signal to the test excitation signal when the polling output signal is equal to or greater than a polling threshold.

* * * * *